(12) United States Patent
Prieur

(10) Patent No.: US 11,760,808 B2
(45) Date of Patent: Sep. 19, 2023

(54) COMPOSITIONS AND METHODS FOR DETECTING AND TREATING OVARIAN CANCER

(71) Applicant: Progastrine et Cancers S.À R.L., Luxembourg (LU)

(72) Inventor: Alexandre Prieur, Montpellier (FR)

(73) Assignee: Progastrine et Cancers S.À R.L., Luxembourg (LU)

( * ) Notice: Subject to any disclaimer, the term of this patent is extended or adjusted under 35 U.S.C. 154(b) by 453 days.

(21) Appl. No.: 16/067,151

(22) PCT Filed: Jan. 2, 2017

(86) PCT No.: PCT/EP2017/050033
§ 371 (c)(1),
(2) Date: Jun. 29, 2018

(87) PCT Pub. No.: WO2017/114972
PCT Pub. Date: Jul. 6, 2017

(65) Prior Publication Data
US 2019/0002582 A1    Jan. 3, 2019

(30) Foreign Application Priority Data

Dec. 31, 2015  (EP) ..................... 15307192
Feb. 5, 2016   (EP) ..................... 16305138

(51) Int. Cl.
| | |
|---|---|
| *G01N 31/00* | (2006.01) |
| *G01N 33/53* | (2006.01) |
| *C07K 16/30* | (2006.01) |
| *G01N 33/574* | (2006.01) |
| *C07K 16/26* | (2006.01) |
| *A61P 35/00* | (2006.01) |
| *A61K 39/00* | (2006.01) |
| *A61K 38/17* | (2006.01) |

(52) U.S. Cl.
CPC .......... *C07K 16/3069* (2013.01); *A61P 35/00* (2018.01); *C07K 16/26* (2013.01); *G01N 33/57449* (2013.01); *A61K 38/1709* (2013.01); *A61K 2039/505* (2013.01); *C07K 2317/24* (2013.01); *C07K 2317/34* (2013.01); *C07K 2317/73* (2013.01); *C07K 2317/76* (2013.01); *G01N 2333/595* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,716,111 A | 12/1987 | Osband et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,585,089 A | 12/1996 | Queen et al. |
| 5,639,641 A | 6/1997 | Pedersen et al. |
| 5,693,761 A | 12/1997 | Queen et al. |
| 5,814,318 A | 9/1998 | Lonberg et al. |
| 5,877,293 A | 3/1999 | Adair et al. |
| 5,886,152 A | 3/1999 | Nakatani et al. |
| 6,054,297 A | 4/2000 | Carter et al. |
| 6,180,370 B1 | 1/2001 | Queen et al. |
| 8,158,128 B2 * | 4/2012 | Grimes .................. A61P 43/00 424/158.1 |
| 10,370,444 B2 * | 8/2019 | Houhou ........... G01N 33/57419 |
| 2010/0272635 A1 | 10/2010 | Rodems et al. |

FOREIGN PATENT DOCUMENTS

| | | |
|---|---|---|
| EP | 0 451 261 | 10/1991 |
| EP | 0 519 596 | 12/1992 |
| EP | 0 566 647 | 10/1993 |
| EP | 0 592 106 | 4/1994 |
| EP | 0 682 040 | 11/1995 |
| EP | 0 939 127 | 9/1999 |
| WO | WO 91/10741 | 7/1991 |
| WO | WO 96/33735 | 10/1996 |
| WO | WO 96/34096 | 10/1996 |
| WO | WO 98/16654 | 4/1998 |
| WO | WO 98/24893 | 6/1998 |
| WO | WO 98/46645 | 10/1998 |
| WO | WO 98/50433 | 11/1998 |
| WO | WO 2006/032980 | 3/2006 |
| WO | WO 2008/076454 | 6/2008 |
| WO | WO-2008076454 A1 * | 6/2008 ......... A61K 38/2207 |
| WO | WO 2011/083088 | 7/2011 |

(Continued)

OTHER PUBLICATIONS

Paul, Fundamental Immunology, 3rd Edition, 1993, pp. 292-295, under the heading "Fv Structure and Diversity in Three Dimensions"). (Year: 1993).*
Bendig M. M. (Methods: A Companion to Methods in Enzymology, 1995; 8:83-93) (Year: 1995).*
Von Solinge et al. (1993, Cancer Research, vol. 53, pp. 1823-1828) (Year: 1993).*
Haygood etal. (World J Stem Cells, Sep. 26, 2014; 6(4): 441-447) (Year: 2014).*
Zhan et al. BioMed research International, vol. 2013, Article Id. 916819, pp. 1-10. (Year: 2013).*
Jones et al., *Replacing the complementarity-determining regions in human antibody with those from a mouse*, 321 Nature 522-525 (May 29, 1986).

(Continued)

Primary Examiner — Lisa V Cook
(74) Attorney, Agent, or Firm — Panitch Schwarze Belisario & Nadel LLP; Erin M. Dunston

(57) ABSTRACT

The present invention relates to methods for the in vitro diagnosis of ovarian cancer, and to compositions and methods for the prevention or the treatment of ovarian cancer. Disclosed are compositions that include an antibody binding to progastrin and disclosed are methods that include the use of an antibody binding to progastrin.

8 Claims, 3 Drawing Sheets

Figure 1:
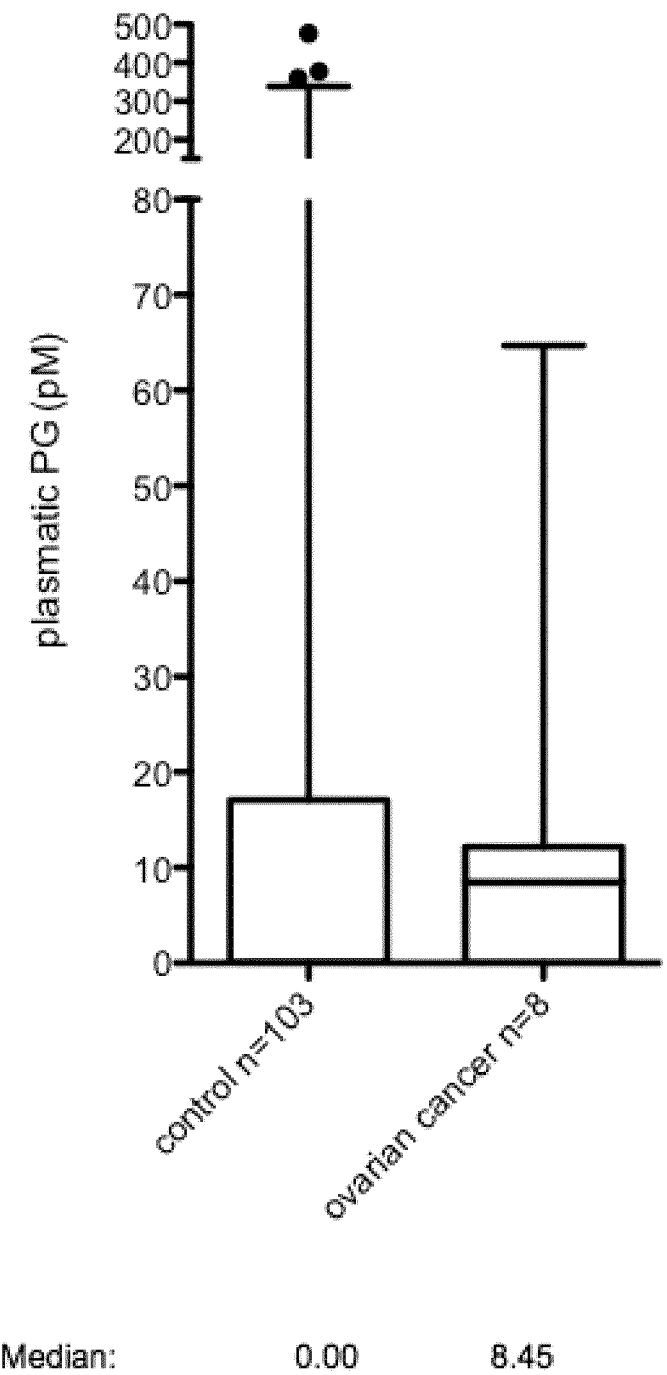

Specification includes a Sequence Listing.

(56) References Cited

FOREIGN PATENT DOCUMENTS

| | | |
|---|---|---|
| WO | WO 2011/083089 | 7/2011 |
| WO | WO 2011/083090 | 7/2011 |
| WO | WO 2011/083091 | 7/2011 |
| WO | WO 2011/116954 | 9/2011 |
| WO | WO 2012/013609 | 2/2012 |

OTHER PUBLICATIONS

Kaas et al., *IMGT/3Dstructure-DB and IMGT/StructuralQuery, a database and a tool for immunoglobulin, T cell receptor and MHC structural data*, 32 Nucleic Acids Research D208-D210 (2004).

Kaas et al., *IMGT Colliers de Perles: Standardized Sequence-Structure Representations of the IgSF and MhcSF Superfamily Domains*, 2 Current Bioinformatics 21-30 (2007).

Kaz ef al., *Epigentic Biomarkers in Esophageal Cancer*, 342(2) Cancer Lett. 1-16 (Jan. 28, 2014).

Kim et al., *Therapeutic strategies in epithelial ovarian cancer*, 31 Journal of Experimental & Clinical Cancer Research 1-8 (2012).

Lefranc, *Unique database numbering system for immunogenetic analysis*, 18(11) Immunology Today 509 (Nov. 1997).

Lefranc et al., *IMGT unique numbering for immunoglobulin and T cell receptor variable domains and Ig superfamily V-like domains*, 27 Developmental and Comparative Immunology 55-77 (2003).

Lefranc, *The IMGT Unique Numbering for Immuoglobulins, T-Cell Receptors, and Ig-Like Domains*, 7 The Immunologist 132-136 (1999).

Macari et al., *TRM6/61 connects PKCα with translational control through $tRNA_i^{Met}$ stabilization: impact on tumorigenesis*, Oncogene 1-12 (2015).

Padlan, *A Possible Procedure for Reducing the Immunogenicity of Antibody Variable Domains While Preserving Their Ligand-Binding Properties*, 28(4/5) Molecular Immunology 489-498 (1991).

Roguska et al., *Humanization of murine monoclonal antibodies through variable domain resurfacing*, 91 Proc. Natl. Acad. Sci. 969-973 (Feb. 1994).

Ruiz et al., *IMGT gene identification and Colliers de Perles of human immunoglobulins with known 3D structures*, 53 Immunogenetics 857-883 (2002).

Singer et al., *Optimal Humanization of 1B4, an Anti-CD18 Murine Monoclonal Antibody, Is Achieved by Correct Choice of Human V-Region Framework Sequences*, 7 The Journal of Immunology 2844-2857 (Apr. 1, 1993).

Studnicka et al., *Human-engineered monoclonal antibodies retain full specific biding activity by preserving non-CDR complementarity-modulating residues*, 6(1) Protein Engineering Design & Selection 805-815 (Jun. 1, 1994) (abstract only).

Van Solinge et al., *Ovarian Cancers Express and Process Progastrin*, 53 Cancer Research 1823-1828 (Apr. 15, 1993).

\* cited by examiner

SEQUENCE LISTING

```
<160> NUMBER OF SEQ ID NOS: 40

<210> SEQ ID NO 1
<211> LENGTH: 80
<212> TYPE: PRT
<213> ORGANISM: Homo sapiens
<220> FEATURE:
<221> NAME/KEY: SITE
<222> LOCATION: (1)..(80)
<223> OTHER INFORMATION: Human progastrin

<400> SEQUENCE: 1

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu Glu
    50                  55                  60

Ala Tyr Gly Trp Met Asp Phe Gly Arg Arg Ser Ala Glu Asp Glu Asn
65                  70                  75                  80

<210> SEQ ID NO 2
<211> LENGTH: 14
<212> TYPE: PRT
<213> ORGANISM: Artificial
```

```
<220> FEATURE:
<223> OTHER INFORMATION: Amino acids 1-14, N-terminal extremity of
      human progastrin

<400> SEQUENCE: 2

Ser Trp Lys Pro Arg Ser Gln Gln Pro Asp Ala Pro Leu Gly
1               5                   10

<210> SEQ ID NO 3
<211> LENGTH: 26
<212> TYPE: PRT
<213> ORGANISM: Artificial
<220> FEATURE:
<223> OTHER INFORMATION: Amino acids 55-80, C-terminal extremity of
      human progastrin

<400> SEQUENCE: 3

Gln Gly Pro Trp Leu Glu Glu Glu Glu Ala Tyr Gly Trp Met Asp
1               5                   10                  15

Phe Gly Arg Arg Ser Ala Glu Asp Glu Asn
            20                  25

<210> SEQ ID NO 4
<211> LENGTH: 8
<212> TYPE: PRT
<213> ORGANISM: Artificial
<220> FEATURE:
<223> OTHER INFORMATION: 6B5B11C10 CDR-H1

<400> SEQUENCE: 4

Gly Tyr Ile Phe Thr Ser Tyr Trp
1               5

<210> SEQ ID NO 5
<211> LENGTH: 8
<212> TYPE: PRT
<213> ORGANISM: Artificial
<220> FEATURE:
<223> OTHER INFORMATION: 6B5B11C10 CDR-H2

<400> SEQUENCE: 5

Phe Tyr Pro Gly Asn Ser Asp Ser
1               5

<210> SEQ ID NO 6
<211> LENGTH: 8
<212> TYPE: PRT
<213> ORGANISM: Artificial
<220> FEATURE:
<223> OTHER INFORMATION: 6B5B11C10 CDR-H3

<400> SEQUENCE: 6

Thr Arg Arg Asp Ser Pro Gln Tyr
1               5

<210> SEQ ID NO 7
<211> LENGTH: 11
<212> TYPE: PRT
<213> ORGANISM: Artificial
<220> FEATURE:
<223> OTHER INFORMATION: 6B5B11C10 CDR-L1

<400> SEQUENCE: 7

Gln Ser Ile Val His Ser Asn Gly Asn Thr Tyr
1               5                   10
```

```
<210> SEQ ID NO 8
<211> LENGTH: 3
<212> TYPE: PRT
<213> ORGANISM: Artificial
<220> FEATURE:
<223> OTHER INFORMATION: 6B5B11C10 CDR-L2

<400> SEQUENCE: 8

Lys Val Ser
1

<210> SEQ ID NO 9
<211> LENGTH: 9
<212> TYPE: PRT
<213> ORGANISM: Artificial
<220> FEATURE:
<223> OTHER INFORMATION: 6B5B11C10 CDR-L3

<400> SEQUENCE: 9

Phe Gln Gly Ser His Val Pro Phe Thr
1               5

<210> SEQ ID NO 10
<211> LENGTH: 7
<212> TYPE: PRT
<213> ORGANISM: Artificial
<220> FEATURE:
<223> OTHER INFORMATION: 20D2C3G2 CDR-H1

<400> SEQUENCE: 10

Gly Tyr Thr Phe Ser Ser Trp
1               5

<210> SEQ ID NO 11
<211> LENGTH: 8
<212> TYPE: PRT
<213> ORGANISM: Artificial
<220> FEATURE:
<223> OTHER INFORMATION: 20D2C3G2 CDR-H2

<400> SEQUENCE: 11

Phe Leu Pro Gly Ser Gly Ser Thr
1               5

<210> SEQ ID NO 12
<211> LENGTH: 11
<212> TYPE: PRT
<213> ORGANISM: Artificial
<220> FEATURE:
<223> OTHER INFORMATION: 20D2C3G2 CDR-H3

<400> SEQUENCE: 12

Ala Thr Asp Gly Asn Tyr Asp Trp Phe Ala Tyr
1               5                   10

<210> SEQ ID NO 13
<211> LENGTH: 11
<212> TYPE: PRT
<213> ORGANISM: Artificial
<220> FEATURE:
<223> OTHER INFORMATION: 20D2C3G2 CDR-L1

<400> SEQUENCE: 13

Gln Ser Leu Val His Ser Ser Gly Val Thr Tyr
1               5                   10

<210> SEQ ID NO 14
```

```
<211> LENGTH: 3
<212> TYPE: PRT
<213> ORGANISM: Artificial
<220> FEATURE:
<223> OTHER INFORMATION: 20D2C3G2 CDR-L2

<400> SEQUENCE: 14

Lys Val Ser
1

<210> SEQ ID NO 15
<211> LENGTH: 9
<212> TYPE: PRT
<213> ORGANISM: Artificial
<220> FEATURE:
<223> OTHER INFORMATION: 20D2C3G2 CDR-L3

<400> SEQUENCE: 15

Ser Gln Ser Thr His Val Pro Pro Thr
1               5

<210> SEQ ID NO 16
<211> LENGTH: 8
<212> TYPE: PRT
<213> ORGANISM: Artificial
<220> FEATURE:
<223> OTHER INFORMATION: 1E9D9B6 CDR-H1

<400> SEQUENCE: 16

Gly Tyr Thr Phe Thr Ser Tyr Tyr
1               5

<210> SEQ ID NO 17
<211> LENGTH: 8
<212> TYPE: PRT
<213> ORGANISM: Artificial
<220> FEATURE:
<223> OTHER INFORMATION: 1E9D9B6 CDR-H2

<400> SEQUENCE: 17

Ile Asn Pro Ser Asn Gly Gly Thr
1               5

<210> SEQ ID NO 18
<211> LENGTH: 10
<212> TYPE: PRT
<213> ORGANISM: Artificial
<220> FEATURE:
<223> OTHER INFORMATION: 1E9D9B6 CDR-H3

<400> SEQUENCE: 18

Thr Arg Gly Gly Tyr Tyr Pro Phe Asp Tyr
1               5                   10

<210> SEQ ID NO 19
<211> LENGTH: 11
<212> TYPE: PRT
<213> ORGANISM: Artificial
<220> FEATURE:
<223> OTHER INFORMATION: 1E9D9B6 CDR-L1

<400> SEQUENCE: 19

Gln Ser Leu Leu Asp Ser Asp Gly Lys Thr Tyr
1               5                   10

<210> SEQ ID NO 20
<211> LENGTH: 3
```

```
<212> TYPE: PRT
<213> ORGANISM: Artificial
<220> FEATURE:
<223> OTHER INFORMATION: 1E9D9B6 CDR-L2

<400> SEQUENCE: 20

Leu Val Ser
1

<210> SEQ ID NO 21
<211> LENGTH: 9
<212> TYPE: PRT
<213> ORGANISM: Artificial
<220> FEATURE:
<223> OTHER INFORMATION: 1E9D9B6 CDR-L3

<400> SEQUENCE: 21

Trp Gln Gly Thr His Ser Pro Tyr Thr
1               5

<210> SEQ ID NO 22
<211> LENGTH: 9
<212> TYPE: PRT
<213> ORGANISM: Artificial
<220> FEATURE:
<223> OTHER INFORMATION: 1B3B4F11 CDR-H1

<400> SEQUENCE: 22

Gly Tyr Ser Ile Thr Ser Asp Tyr Ala
1               5

<210> SEQ ID NO 23
<211> LENGTH: 7
<212> TYPE: PRT
<213> ORGANISM: Artificial
<220> FEATURE:
<223> OTHER INFORMATION: 1B3B4F11 CDR-H2

<400> SEQUENCE: 23

Ile Ser Phe Ser Gly Tyr Thr
1               5

<210> SEQ ID NO 24
<211> LENGTH: 14
<212> TYPE: PRT
<213> ORGANISM: Artificial
<220> FEATURE:
<223> OTHER INFORMATION: 1B3B4F11 CDR-H3

<400> SEQUENCE: 24

Ala Arg Glu Val Asn Tyr Gly Asp Ser Tyr His Phe Asp Tyr
1               5                   10

<210> SEQ ID NO 25
<211> LENGTH: 7
<212> TYPE: PRT
<213> ORGANISM: Artificial
<220> FEATURE:
<223> OTHER INFORMATION: 1B3B4F11 CDR-L1

<400> SEQUENCE: 25

Ser Gln His Arg Thr Tyr Thr
1               5

<210> SEQ ID NO 26
<211> LENGTH: 7
<212> TYPE: PRT
```

<213> ORGANISM: Artificial
<220> FEATURE:
<223> OTHER INFORMATION: 1B3B4F11 CDR-L2

<400> SEQUENCE: 26

Val Lys Lys Asp Gly Ser His
1               5

<210> SEQ ID NO 27
<211> LENGTH: 13
<212> TYPE: PRT
<213> ORGANISM: Artificial
<220> FEATURE:
<223> OTHER INFORMATION: 1B3B4F11 CDR-L3

<400> SEQUENCE: 27

Gly Val Gly Asp Ala Ile Lys Gly Gln Ser Val Phe Val
1               5                   10

<210> SEQ ID NO 28
<211> LENGTH: 8
<212> TYPE: PRT
<213> ORGANISM: Artificial
<220> FEATURE:
<223> OTHER INFORMATION: 1C10D3B9 CDR-H1

<400> SEQUENCE: 28

Gly Phe Thr Phe Thr Thr Tyr Ala
1               5

<210> SEQ ID NO 29
<211> LENGTH: 8
<212> TYPE: PRT
<213> ORGANISM: Artificial
<220> FEATURE:
<223> OTHER INFORMATION: 1C10D3B9 CDR-H2

<400> SEQUENCE: 29

Ile Ser Ser Gly Gly Thr Tyr Thr
1               5

<210> SEQ ID NO 30
<211> LENGTH: 10
<212> TYPE: PRT
<213> ORGANISM: Artificial
<220> FEATURE:
<223> OTHER INFORMATION: 1C10D3B9 CDR-H3

<400> SEQUENCE: 30

Ala Thr Gln Gly Asn Tyr Ser Leu Asp Phe
1               5                   10

<210> SEQ ID NO 31
<211> LENGTH: 11
<212> TYPE: PRT
<213> ORGANISM: Artificial
<220> FEATURE:
<223> OTHER INFORMATION: 1C10D3B9 CDR-L1

<400> SEQUENCE: 31

Lys Ser Leu Arg His Thr Lys Gly Ile Thr Phe
1               5                   10

<210> SEQ ID NO 32
<211> LENGTH: 3
<212> TYPE: PRT
<213> ORGANISM: Artificial

<220> FEATURE:
<223> OTHER INFORMATION: 1C10D3B9 CDR-L2

<400> SEQUENCE: 32

Gln Met Ser
1

<210> SEQ ID NO 33
<211> LENGTH: 9
<212> TYPE: PRT
<213> ORGANISM: Artificial
<220> FEATURE:
<223> OTHER INFORMATION: 1C10D3B9 CDR-L3

<400> SEQUENCE: 33

Ala Gln Asn Leu Glu Leu Pro Leu Thr
1               5

<210> SEQ ID NO 34
<211> LENGTH: 8
<212> TYPE: PRT
<213> ORGANISM: Artificial
<220> FEATURE:
<223> OTHER INFORMATION: 2C6C3C7 CDR-H1

<400> SEQUENCE: 34

Gly Phe Ile Phe Ser Ser Tyr Gly
1               5

<210> SEQ ID NO 35
<211> LENGTH: 8
<212> TYPE: PRT
<213> ORGANISM: Artificial
<220> FEATURE:
<223> OTHER INFORMATION: 2C6C3C7 CDR-H2

<400> SEQUENCE: 35

Ile Asn Thr Phe Gly Asp Arg Thr
1               5

<210> SEQ ID NO 36
<211> LENGTH: 7
<212> TYPE: PRT
<213> ORGANISM: Artificial
<220> FEATURE:
<223> OTHER INFORMATION: 2C6C3C7 CDR-H3

<400> SEQUENCE: 36

Ala Arg Gly Thr Gly Thr Tyr
1               5

<210> SEQ ID NO 37
<211> LENGTH: 11
<212> TYPE: PRT
<213> ORGANISM: Artificial
<220> FEATURE:
<223> OTHER INFORMATION: 2C6C3C7 CDR-L1

<400> SEQUENCE: 37

Gln Ser Leu Leu Asp Ser Asp Gly Lys Thr Tyr
1               5                   10

<210> SEQ ID NO 38
<211> LENGTH: 3
<212> TYPE: PRT
<213> ORGANISM: Artificial
<220> FEATURE:

```
<223> OTHER INFORMATION: 2C6C3C7 CDR-L2

<400> SEQUENCE: 38

Leu Val Ser
1

<210> SEQ ID NO 39
<211> LENGTH: 9
<212> TYPE: PRT
<213> ORGANISM: Artificial
<220> FEATURE:
<223> OTHER INFORMATION: 2C6C3C7 CDR-L3

<400> SEQUENCE: 39

Trp Gln Gly Thr His Phe Pro Gln Thr
1               5

<210> SEQ ID NO 40
<211> LENGTH: 10
<212> TYPE: PRT
<213> ORGANISM: Artificial
<220> FEATURE:
<223> OTHER INFORMATION: Amino acids 71-80 of progastrin

<400> SEQUENCE: 40

Phe Gly Arg Arg Ser Ala Glu Asp Glu Asn
1               5                   10
```

COMPOSITIONS AND METHODS FOR DETECTING AND TREATING OVARIAN CANCER

CROSS-REFERENCE TO RELATED APPLICATIONS

This application is a U.S. National Stage Application pursuant to 35 U.S.C. § 371 of International Patent Application PCT/EP2017/050033, filed on Jan. 2, 2017, and published as WO 2017/114972 on Jul. 6, 2017, which claims priority to European Patent Application 16305138.6, filed on Feb. 5, 2016, and European Patent Application 15307192.3, filed on Dec. 31, 2015, all of which are incorporated herein by reference in their entireties for all purposes.

INTRODUCTION

The present invention relates to the in vitro diagnosis, the prevention and the treatment of cancer, more particularly it relates to methods for the in vitro diagnosis of ovarian cancer, and to methods and compositions for the prevention or the treatment of ovarian cancer. Compositions according to the invention comprise a progastrin-binding molecule, in particularly an anti-hPG antibody, whereas methods according to the invention comprise the use of a progastrin-binding molecule, and particularly to an anti-hPG antibody.

Ovarian cancer arises from ovarian cells, in the tractus between throat and stomach, and has been described as the eighth most common cancer, affecting more men than women and with rates varying widely among countries.

The two most common types of ovarian cancer are ovarian squamous-cell carcinoma and ovarian adenocarcinoma. A number of more rare subtypes are also known. Squamous-cell carcinoma arises from the epithelial cells of the esophagus, whereas adenocarcinoma arises from glandular cells present in the lower part of esophagus.

Clinical diagnosis is based on a biopsy, which is usually performed under computerized tomography scan or ultrasound. The poor outcome of this illness is due in particular to a late diagnosis, due in particular to the absence of early signs and symptoms. To date, there are no molecular biomarkers that have been translated to widespread clinical practice of ovarian cancer (Kaz et al, Cancer Letters, 2014). Treatments depend on the development of the cancer, and usually include surgery, for small-localized tumors, or chemotherapy, possibly in combination with radiation therapy.

Therefore, there is still a need for methods allowing a quick, reliable and cost-effective diagnosis of ovarian cancer, as there is still a need for new compositions and methods for the prevention or the treatment of ovarian cancer.

DESCRIPTION

This is the object of the present invention.

The present invention now provides methods for the in vitro diagnosis of ovarian cancer, wherein said method comprises the detection of progastrin in a biological sample from a subject. Preferably, the amount of progastrin in said sample is determined, thus allowing quantification of progastrin. The present invention also provides a composition for use in the prevention or the treatment of ovarian cancer, wherein said composition comprises an antibody binding to progastrin, and methods for the prevention or the treatment of ovarian cancer comprising the use of a composition comprising an antibody binding to progastrin, alone or in combination with any other known prevention or therapeutic methods against ovarian cancer.

Human pre-progastrin, a 101 amino acids peptide (Amino acid sequence reference: AAB19304.1), is the primary translation product of the gastrin gene. Progastrin is formed by cleavage of the first 21 amino acids (the signal peptide) from preprogastrin. The 80 amino acid chain of progastrin is further processed by cleavage and modifying enzymes to several biologically active gastrin hormone forms: gastrin 34 (G34) and glycine-extended gastrin 34 (G34-Gly), comprising amino acids 38-71 of progastrin, gastrin 17 (G17) and glycine-extended gastrin 17 (G17-Gly), comprising amino acids 55 to 71 of progastrin.

Anti-human progastrin (anti-hPG) monoclonal antibodies and their use for diagnosis or therapy have been described in the following documents: WO 2011/083 088 for colorectal cancer, WO 2011/083 090 for breast cancer, WO 2011/083 091 for pancreatic cancer, WO 2011/116 954 for colorectal and gastrointestinal cancer, and WO 2012/013 609 and WO 2011/083089 for liver pathologies.

The present invention will become more fully understood from the detailed description given herein and from the accompanying drawings, which are given by way of illustration only and do not limit the intended scope of the invention.

In a first aspect, the present invention relates to a method for the in vitro evaluation of a risk of the presence of ovarian cancer, wherein said method comprises a step of detecting progastrin in a biological sample from a subject. The presence of progestin in the sample indicates that there is a risk of the presence of ovarian cancer.

The present inventors were the first to show that progastrin levels are more elevated in the ovarian-cancer patients than in healthy subjects. In contrast, previous studies concluded that the physiological significance of ovarian gastrin expression is difficult to assess (von Solinge et al., Cancer Res., 1993, 53(8): 1823-1828).

Thus, in a first embodiment, the invention relates to an in vitro method for evaluating the risk of the presence of ovarian cancer in a subject, said method comprising the steps of:

a) contacting a biological sample from said subject with at least one progastrin-binding molecule, and b) detecting the binding of said progastrin-binding molecule to progastrin in said sample, wherein said binding indicates a risk of the presence of ovarian cancer.

The binding of progastrin-binding molecule may be detected by various assays available to the skilled artisan. Although any suitable means for carrying out the assays are included within the invention, it can be mentioned in particular FACS, ELISA, RIA, western-blot and IHC.

In a preferred embodiment, the method according to the invention for the in vitro evaluation of a risk of the presence of ovarian cancer in a subject comprises the steps of:

a) contacting said biological sample with at least one progastrin-binding molecule, b) determining the concentration of progastrin in said biological sample, wherein a concentration of progastrin of at least 5 pM in said biological sample is indicative of a risk of the presence of ovarian cancer.

Once the concentration of progastrin present in the sample is determined, the result can be compared with those of control sample(s), which is (are) obtained in a manner similar to the test samples but from individual(s)s known not to suffer from a ovarian cancer. If the concentration of progastrin is significantly more elevated in the test sample, it may be concluded that there is an increased likelihood that the subject from whom it was derived has an ovarian cancer.

Thus, in a more preferred embodiment, the method of the invention comprises the further steps of:
- c) determining a reference concentration of progastrin in a reference sample,
- d) comparing the concentration of progastrin in said biological sample with said reference concentration of progastrin,
- e) evaluating, from the comparison of step d), the risk of the presence of ovarian cancer.

According to another aspect, the invention relates to an in vitro method for diagnosing ovarian cancer in a subject, said method comprising the steps of:
- a) contacting a biological sample from said subject with at least one progastrin-binding molecule, and
- b) detecting the binding of said progastrin-binding molecule to progastrin in said sample, wherein said binding indicated the presence of ovarian cancer in said subject.

In a preferred embodiment, the present invention relates to a method for the in vitro diagnosis of ovarian cancer in a subject, comprising the steps of:
- a) contacting said biological sample with at least one progastrin-binding molecule,
- b) determining the level or concentration of progastrin in said biological sample, wherein a concentration of progastrin of at least 5 pM in said biological sample is indicative of the presence of ovarian cancer in said subject.

In a more particular embodiment of a method according to the invention, a concentration of progastrin of at least 5 pM, 10 pM, at least 20 pM, at least 30 pM, in said biological sample is indicative of the presence of ovarian cancer in said subject.

In a more preferred embodiment, the method of the invention comprises the further steps of:
- c) determining a reference concentration of progastrin in a reference sample,
- d) comparing the concentration of progastrin in said biological sample with said reference level or concentration of progastrin,
- e) diagnosing, from the comparison of step d), the presence of ovarian cancer.

According to another aspect, the invention relates to an in vitro method for diagnosing metastasized ovarian cancer in a subject, said method comprising the steps of:
- a) contacting a biological sample from said subject with at least one progastrin-binding molecule, and
- b) detecting the binding of said progastrin-binding molecule to progastrin in said sample, wherein said binding indicates the presence of metastasized ovarian cancer in said subject.

In a preferred embodiment, the present invention relates to a method for the in vitro diagnosis of metastasized ovarian cancer in a subject, from a biological sample of said subject, comprising the steps of:
- a) contacting said biological sample with at least one progastrin-binding molecule,
- b) determining by a biochemical assay the level or concentration of progastrin in said biological sample, wherein a concentration of progastrin of at least 5 pM higher in said biological sample is indicative of the presence of metastasized ovarian cancer in said subject.

In a more particular embodiment of a method according to the invention, a concentration of progastrin of at least 5 pM, 10 pM, at least 20 pM, at least 30 pM, at least 40 pM or at least 50 pM in said biological sample is indicative of the presence of metastasized ovarian cancer in said subject.

In a more preferred embodiment, the method of the invention comprises the further steps of:
- c) determining a reference concentration of progastrin in a reference sample,
- d) comparing the concentration of progastrin in said biological sample with said reference level or concentration of progastrin,
- e) diagnosing, from the comparison of step d), the presence of metastasized ovarian cancer.

In a particular embodiment, the present invention relates to a method for the in vitro diagnosis of ovarian cancer in a subject, comprising the determination of the concentration of progastrin in a biological sample and comparing said value obtained to the concentration of progastrin in a reference sample.

In a more particular embodiment, in a method for the diagnosis of ovarian cancer according to the present invention, the biological sample of said subject is contacted with at least one progastrin-binding molecule, wherein said progastrin-binding molecule is an antibody, or an antigen-binding fragment thereof.

The expression "evaluation of a risk of the presence of ovarian cancer in a subject" designates the determination of a relative probability for a given subject to suffer from ovarian cancer, when compared to a reference subject or value. A method according to the invention represents a tool in the evaluation of said risk, in combination with other methods or indicators such as clinical examination, biopsy and determination of the level of a known biomarker of ovarian cancer.

According to a particular embodiment, the present invention relates to an in vitro diagnosis method of ovarian cancer comprising the determination of the concentration of progastrin in a biological sample from a subject, wherein said subject exhibits at least one clinical symptom of ovarian cancer. Clinical symptoms of ovarian cancer include weight loss, painful or difficult swallowing, cough, indigestion and heartburn.

According to another particular embodiment, the present invention relates to an in vitro diagnosis method of ovarian cancer comprising the determination of the concentration of progastrin in a biological sample from a subject, wherein said subject exhibits at least one clinical symptom of cancer and/or of metastasis.

The expression "in vitro diagnosis" means to determine if a subject is suffering from a particular affection.

Therefore, a method for the in vitro diagnosis of ovarian cancer, according to the present invention can be considered as a tool within a diagnosis process.

In a more particular embodiment, the present invention relates to a method for the in vitro diagnosis of ovarian cancer in a subject, comprises the determination of the concentration of progastrin in said biological sample and the determination of a known biomarker of ovarian cancer.

The term "progastrin" designates the mammalian progastrin peptide, and particularly human progastrin. For the avoidance of doubt, without any specification, the expression "human progastrin" refers to the human PG of sequence SEQ ID No. 1. Human progastrin comprises notably a N-terminus and a C-terminus domains which are not present in the biologically active gastrin hormone forms mentioned above. Preferably, the sequence of said N-terminus domain is represented by SEQ ID NO. 2. In another preferred embodiment, the sequence of said C-terminus domain is represented by SEQ ID NO. 3.

The determination of the concentration of progastrin, in a method according to the invention, is performed by any method known by one skilled in the art of biochemistry.

Preferably, determining the levels of progastrin in a sample includes contacting said sample with a progastrin-binding molecule and measuring the binding of said progastrin-binding molecule to progastrin.

When expression levels are measured at the protein level, it may be notably performed using specific progastrin-binding molecules, such as e.g., antibodies, in particular using well known technologies such as cell membrane staining using biotinylation or other equivalent techniques followed by immunoprecipitation with specific antibodies, western blot, ELISA or ELISPOT, enzyme-linked immunosorbant assays (ELISA), radioimmunoassays (RIA), immunohistochemistry (IHC), immunofluorescence (IF), antibodies microarrays, or tissue microarrays coupled to immunohistochemistry. Other suitable techniques include FRET or BRET, single cell microscopic or histochemistry methods using single or multiple excitation wavelength and applying any of the adapted optical methods, such as electrochemical methods (voltametry and amperometry techniques), atomic force microscopy, and radio frequency methods, e.g. multipolar resonance spectroscopy, confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry), cell ELISA, flow cytometry, radioisotopic, magnetic resonance imaging, analysis by polyacrylamide gel electrophoresis (SDS-PAGE); HPLC-Mass Spectroscopy; Liquid Chromatography/Mass Spectrometry/Mass Spectrometry (LC-MS/MS)). All these techniques are well known in the art and need not be further detailed here. These different techniques can be used to measure the progastrin levels.

Said method may in particular be chosen among: a method based on immuno-detection, a method based on western blot, a method based on mass spectrometry, a method based on chromatography, and a method based on flow cytometry. Although any suitable means for carrying out the assays are included within the invention, methods such as FACS, ELISA, RIA, western-blot and IHC are particularly useful for carrying out the method of the invention.

In a more particular embodiment, a method for the in vitro diagnosis of ovarian cancer according to the invention comprises contacting a biological sample from a subject with a progastrin binding molecule using an immunoenzymatic assay, preferably based on techniques chosen among RIA and ELISA.

A "biological sample" as used herein is a sample of biological tissue or fluid that contains nucleic acids or polypeptides, e.g., of an ovarian cancer protein, polynucleotide or transcript. Such a sample must allow for the determination of the expression levels of progastrin. Progastrin is known to be a secreted protein. Preferred biological samples for the determination of the level of the progastrin protein thus include biological fluids. A "biological fluid" as used herein means any fluid that includes material of biological origin. Preferred biological fluids for use in the present invention include bodily fluids of an animal, e.g. a mammal, preferably a human subject. The bodily fluid may be any bodily fluid, including but not limited to blood, plasma, serum, lymph, cerebrospinal fluid (CSF), saliva, sweat and urine. Preferably, said preferred liquid biological samples include samples such as a blood sample, a plasma sample, or a serum sample. More preferably, the biological sample is a blood sample. Indeed, such a blood sample may be obtained by a completely harmless blood collection from the patient and thus allows for a non-invasive assessment of the risks that the subject will develop a tumor.

A "biological sample" as used herein also includes a solid cancer sample of the patient to be tested, when the cancer is a solid cancer. Such solid cancer sample allows the skilled person to perform any type of measurement of the level of the biomarker of the invention. In some cases, the methods according to the invention may further comprise a preliminary step of taking a solid cancer sample from the patient. By a "solid cancer sample", it is referred to a tumor tissue sample. Even in a cancerous patient, the tissue which is the site of the tumor still comprises non tumor healthy tissue. The "cancer sample" should thus be limited to tumor tissue taken from the patient. Said "cancer sample" may be a biopsy sample or a sample taken from a surgical resection therapy.

A biological sample is typically obtained from a eukaryotic organism, most preferably a mammal, or a bird, reptile, or fish. Indeed, a "subject" which may be subjected to the method described herein may be any of mammalian animals including human, dog, cat, cattle, goat, pig, swine, sheep and monkey; or a bird; reptile; or fish. Preferably, a subject is a human being; a human subject may be known as a "patient".

By "obtaining a biological sample," it is herein meant to obtain a biological sample for use in methods described in this invention. Most often, this will be done by removing a sample of cells from an animal, but can also be accomplished by using previously isolated cells (e.g., isolated by another person, at another time, and/or for another purpose), or by performing the methods of the invention in vivo. Archival tissues, having treatment or outcome history, will be particularly useful.

This sample may be obtained and if necessary prepared according to methods known to a person skilled in the art. In particular, it is well known in the art that the sample should be taken from a fasting subject.

The determination of the concentration of progastrin relates to the determination of the quantity of progastrin in known volume of a sample. The concentration of progastrin may be expressed relatively to a reference sample, for example as a ratio or a percentage. The concentration may also be expressed as the intensity or localization of a signal, depending on the method used for the determination of said concentration. Preferably, the concentration of a compound in a sample is expressed after normalization of the total concentration of related compounds in said sample, for example the level or concentration of a protein is expressed after normalization of the total concentration of proteins in the sample.

Preferably, the risk that said subject suffers from ovarian cancer is determined by comparing the level of progastrin measured in said biological sample with a reference level.

The term "reference level", as used herein, refers to the expression level of the ovarian cancer marker under consideration, i.e. progastrin, in a reference sample. A "reference sample", as used herein, means a sample obtained from subjects, preferably two or more subjects, known to be free of the disease or, alternatively, from the general population. The suitable reference expression levels of progastrin can be determined by measuring the expression levels of said marker in several suitable subjects, and such reference levels can be adjusted to specific subject populations. The reference value or reference level can be an absolute value; a relative value; a value that has an upper or a lower limit; a range of values; an average value; a median value, a mean value, or a value as compared to a particular control or baseline value. A reference value can be based on an individual sample value such as, for example, a value obtained from a sample from the subject being tested, but at an earlier point in time. The reference value can be based on a large number of samples, such as from population of subjects of the chronological age matched group, or based on a pool of samples including or excluding the sample to be tested.

Advantageously, a "reference level" is a predetermined progastrin level, obtained from a biological sample from a subject with a known particular status as regards cancer. In particular embodiments, the reference level used for comparison with the test sample in step (b) may have been obtained from a biological sample from a healthy subject, or from a biological sample from a subject suffering from cancer; it is understood that the reference expression profile can also be obtained from a pool of biological samples of healthy subjects or from a pool of samples from subjects having cancer.

In a particular embodiment of the method of the invention, the reference sample is collected from subjects exempt from any cancer, and preferably from any pathology. It is to be understood that, according to the nature of the biological sample collected from a patient, the reference sample will be a biological sample of the same nature of said biological sample.

The level of progastrin is determined in the present method by determining the amount of progastrin which is bound by a progastrin-binding molecule, preferably by an antibody recognising progastrin.

By "progastrin-binding molecule", it is herein referred to any molecule that binds progastrin, but does not bind gastrin-17 (G17), gastrin-34 (G34), glycine-extended gastrin-17 (G17-Gly), or glycine-extended gastrin-34 (G34-Gly). The progastrin-binding molecule of the present invention may be any progastrin-binding molecule, such as, for instance, an antibody molecule or a receptor molecule. Preferably, the progastrin-binding molecule is an anti-progastrin antibody or an antigen-binding fragment thereof.

By "binding", "binds", or the like, it is intended that the antibody, or antigen binding fragment thereof, forms a complex with an antigen which, under physiologic conditions, is relatively stable. Methods for determining whether two molecules bind are well known in the art and include, for example, equilibrium dialysis, surface plasmon resonance, and the like. In a particular embodiment, said antibody, or antigen-binding fragment thereof, binds to progastrin with an affinity that is at least two-fold greater than its affinity for binding to a non-specific molecule such as BSA or casein. In a more particular embodiment, said antibody, or antigen-binding fragment thereof, binds only to progastrin.

In a particular embodiment, in a method for the diagnosis of ovarian cancer according to the invention, a biological sample from the subject is contact with at least one progastrin-binding molecule, wherein the affinity of said molecule for progastrin is at least 100 nM, at least 90 nM, at least 80 nM, at least 70 nM, at least 60 nM, at least 50 nM, at least 40 nM, at least 30 nM, at least 20 nM, at least 10 nM, at least 5 nM, at least 1 nM, at least 100 pM, at least 10 pM, or at least 1 pM, as determined by a method such as above-described.

In a particular embodiment, the present invention relates to a method for the diagnosis of ovarian cancer, comprising the detection of the concentration of progastrin in a biological sample from a subject, wherein said biological sample is contacted with an anti-hPG antibody, or an antigen-binding fragment thereof.

The term "antibody" as used herein is intended to include polyclonal and monoclonal antibodies. An antibody (or "immunoglobulin") consists of a glycoprotein comprising at least two heavy (H) chains and two light (L) chains interconnected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed "complementarity determining regions" (CDR) or "hypervariable regions", which are primarily responsible for binding an epitope of an antigen, and which are interspersed with regions that are more conserved, termed framework regions (FR). Method for identifying the CDRs within light and heavy chains of an antibody and determining their sequence are well known to the skilled person. For the avoidance of doubt, in the absence of any indication in the text to the contrary, the expression CDRs means the hypervariable regions of the heavy and light chains of an antibody as defined by IMGT, wherein the IMGT unique numbering provides a standardized delimitation of the framework regions and of the complementary determining regions, CDR1-IMGT: 27 to 38, CDR2.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommie, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system. Antibodies can be of different isotypes (namely IgA, IgD, IgE, IgG or IgM).

In a more particular embodiment, said progastrin-binding antibody, or an antigen-binding fragment thereof, is selected from the group consisting of: polyclonal antibodies, monoclonal antibodies, chimeric antibodies, single chain antibodies, camelized antibodies, IgA1 antibodies, IgA2 antibodies, IgD antibodies, IgE antibodies, IgG1 antibodies, IgG2 antibodies, IgG3 antibodies, IgG4 antibodies and IgM antibodies.

A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

The term "monoclonal antibody" designates an antibody arising from a nearly homogeneous antibody population, wherein population comprises identical antibodies except for a few possible naturally-occurring mutations which can be found in minimal proportions. A monoclonal antibody arises from the growth of a single cell clone, such as a hybridoma, and is characterized by heavy chains of one class and subclass, and light chains of one type.

By the expression "antigen-binding fragment" of an antibody, it is intended to indicate any peptide, polypeptide, or protein retaining the ability to bind to the target (also generally referred to as antigen) of the said antibody, generally the same epitope, and comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, or at least 200 contiguous amino acid residues, of the amino acid sequence of the antibody.

In a particular embodiment, the said antigen-binding fragment comprises at least one CDR of the antibody from which it is derived. Still in a preferred embodiment, the said antigen-binding fragment comprises 2, 3, 4 or 5 CDRs, more preferably the 6 CDRs of the antibody from which it is derived.

The "antigen-binding fragments" can be selected, without limitation, in the group consisting of Fv, scFv (sc for single chain), Fab, F(ab')$_2$, Fab', scFv-Fc fragments or diabodies, or fusion proteins with disordered peptides such as XTEN (extended recombinant polypeptide) or PAS motifs, or any fragment of which the half-life time would be increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome, said fragments having at least one of the characteristic CDRs of the antibody according to the invention. Preferably, said "antigen-binding fragments" will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of the affinity of the antibody from which it is descended, with respect to the target.

In another particular embodiment, in a method for the diagnosis of ovarian cancer according to the invention, a biological sample from a subject is contacted with an antibody binding to progastrin, wherein said antibody has been obtained by an immunization method known by a person skilled in the art, wherein using as an immunogen a peptide which amino acid sequence comprises the totality or a part of the amino-acid sequence of progastrin. More particularly, said immunogen comprises a peptide chosen among:

a peptide which amino acid sequence comprises, or consists of, the amino acid sequence of full length progastrin, and particularly full length human progastrin of SEQ ID N° 1, a peptide which amino acid sequence corresponds to a part of the amino acid sequence of progastrin, and particularly full length human progastrin of SEQ ID N° 1, a peptide which amino acid sequence corresponds to a part or to the whole amino acid sequence of the N-terminal part of progastrin, and in particular peptides comprising, or consisting of, the amino acid sequence:

(SEQ ID No 2)
SWKPRSQQPDAPLG, and a peptide which amino acid sequence corresponds to a part or to the whole amino acid sequence of the C-terminal part of progastrin, and in particular peptides comprising, or consisting of, the amino acid sequence:

(SEQ ID No 3)
QGPWLEEEEEAYGWMDFGRRSAEDEN, a peptide which amino acid sequence corresponds to a part of the amino acid sequence of the C-terminal part of progastrin, and in particular peptides comprising the amino acid sequence FGRRSAEDEN (SEQ ID N° 40) corresponding to amino acids 71-80 of progastrin The skilled person will realize that such immunization may be used to generate either polyclonal or monoclonal antibodies, as desired. Methods for obtaining each of these types of antibodies are well known in the art. The skilled person will thus easily select and implement a method for generating polyclonal and/or monoclonal antibodies against any given antigen.

Examples of monoclonal antibodies which were generated by using an immunogen comprising the amino-acid sequence "SWKPRSQQPDAPLG", corresponding to the amino acid sequence 1-14 of human progastrin (N-terminal extremity) include, but are not restricted to, monoclonal antibodies designated as: mAb3, mAb4, mAb16, and mAb19 and mAb20, as described in the following Table 1 to Table 4. Other monoclonal antibodies have been described, although it is not clear whether these antibodies actually bind progastrin (WO 2006/032980). Experimental results of epitope mapping show that mAb3, mAb4, mAb16, and mAb19 and mAb20 do specifically bind an epitope within said hPG N-terminal amino acid sequence. Polyclonal antibodies recognizing specifically an epitope within the N-terminus of progastrin represented by SEQ ID NO. 2, have been described in the art (see e.g, WO 2011/083088).

TABLE 1

| Hybridoma deposit | mAb | Amino acid sequences | | SEQ ID No |
|---|---|---|---|---|
| 6B5B11C10 | mAb3 | VH CDR 1 | GYIFTSYW | SEQ ID No 4 |
| | | VH CDR 2 | FYPGNSDS | SEQ ID No 5 |
| | | VH CDR 3 | TRRDSPQY | SEQ ID No 6 |
| | | VL CDR 1 | QSIVHSNGNTY | SEQ ID No 7 |
| | | VL CDR 2 | KVS | SEQ ID No 8 |
| | | VL CDR 3 | FQGSHVPFT | SEQ ID No 9 |

TABLE 2

| Hybridoma deposit | mAb | Amino acid sequences | | SEQ ID No |
|---|---|---|---|---|
| 20D2C3G2 | mAb4 | VH CDR 1 | GYTFSSW | SEQ ID No 10 |
| | | VH CDR 2 | FLPGSGST | SEQ ID No 11 |
| | | VH CDR 3 | ATDGNYDWFAY | SEQ ID No 12 |
| | | VL CDR 1 | QSLVHSSGVTY | SEQ ID No 13 |
| | | VL CDR 2 | KVS | SEQ ID No 14 |
| | | VL CDR 3 | SQSTHVPPT | SEQ ID No 15 |

TABLE 3

| Hybridoma deposit | mAb | Amino acid sequences | | SEQ ID No |
|---|---|---|---|---|
| 1E9D9B6 | mAb16 | VH CDR 1 | GYTFTSYY | SEQ ID No 16 |
| | | VH CDR 2 | INPSNGGT | SEQ ID No 17 |
| | | VH CDR 3 | TRGGYYPFDY | SEQ ID No 18 |
| | | VL CDR 1 | QSLLDSDGKTY | SEQ ID No 19 |
| | | VL CDR 2 | LVS | SEQ ID No 20 |
| | | VL CDR 3 | WQGTHSPYT | SEQ ID No 21 |

TABLE 4

| Hybridoma deposit | mAb | Amino acid sequences | | SEQ ID No |
|---|---|---|---|---|
| 1B3B4F11 | mAb19 | VH CDR 1 | GYSITSDYA | SEQ ID No 22 |
| | | VH CDR 2 | ISFSGYT | SEQ ID No 23 |
| | | VH CDR 3 | AREVNYGDSYHFDY | SEQ ID No 24 |
| | | VL CDR 1 | SQHRTYT | SEQ ID No 25 |
| | | VL CDR 2 | VKKDGSH | SEQ ID No 26 |
| | | VL CDR 3 | GVGDAIKGQSVFV | SEQ ID No 27 |

Examples of monoclonal antibodies that can be generated by using an immunogen comprising the amino-acid sequence "QGPWLEEEEEAYGWMDFGRRSAEDEN", (C-terminal part of progastrin) corresponding to the amino acid sequence 55-80 of human progastrin include, but are not restricted to antibodies designated as: mAb8 and mAb13 in the following Table 5 and 6. Experimental results of epitope mapping show that mAb13 do specifically bind an epitope within said hPG C-terminal amino acid sequence.

TABLE 5

| Hybridoma deposit | mAb | Amino acid sequences | | SEQ ID No |
|---|---|---|---|---|
| 1C10D3B9 | mAb8 | VH CDR 1 | GFTFTTYA | SEQ ID No 28 |
| | | VH CDR 2 | ISSGGTYT | SEQ ID No 29 |
| | | VH CDR 3 | ATQGNYSLDF | SEQ ID No 30 |
| | | VL CDR 1 | KSLRHTKGITF | SEQ ID No 31 |

TABLE 5-continued

| Hybridoma deposit | mAb | Amino acid sequences | | SEQ ID No |
|---|---|---|---|---|
| | | VL CDR 2 | QMS | SEQ ID No 32 |
| | | VL CDR 3 | AQNLELPLT | SEQ ID No 33 |

TABLE 6

| Hybridoma deposit | mAb | Amino acid sequences | | SEQ ID No |
|---|---|---|---|---|
| 2C6C3C7 | mAb13 | VH CDR 1 | GFIFSSYG | SEQ ID No 34 |
| | | VH CDR 2 | INTFGDRT | SEQ ID No 35 |
| | | VH CDR 3 | ARGTGTY | SEQ ID No 36 |
| | | VL CDR 1 | QSLLDSDGKTY | SEQ ID No 37 |
| | | VL CDR 2 | LVS | SEQ ID No 38 |
| | | VL CDR 3 | WQGTHFPQT | SEQ ID No 39 |

Other examples include anti-hPG monoclonal and/or polyclonal antibodies generated by using an immunogen comprising an amino acid sequence of SEQ ID N° 40.

In a more particular embodiment, in a method according to the invention said biological sample is contacted with an anti-hPG antibody or antigen-binding fragment thereof, wherein said anti-hPG antibody is chosen among N-terminal anti-hPG antibodies and C-terminal anti-hPG antibodies.

The terms "N-terminal anti-hPG antibodies" and "C-terminal anti-hPG antibodies" designate antibodies binding to an epitope comprising amino acids located in the N-terminal part of hPG or to an epitope comprising amino acids located in the C-terminal part of hPG, respectively. Preferably, the term "N-terminal anti-hPG antibodies" refers to antibodies binding to an epitope located in a domain of progastrin whose sequence is represented by SEQ ID NO. 2. In another preferred embodiment, the term "C-terminal anti-hPG antibodies" refers to antibodies binding to an epitope located in a domain of progastrin whose sequence is represented by SEQ ID NO. 3.

The term "epitope" refers to a region of an antigen that is bound by an antibody. Epitopes may be defined as structural or functional. Functional epitopes are generally a subset of the structural epitopes and have those amino acids that directly contribute to the affinity of the interaction. Epitopes may also be conformational. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. The determination of the epitope bound by an antibody may be performed by any epitope mapping technique, known by a person skilled in the art. An epitope may comprise different amino acids, which located sequentially within the amino acid sequence of a protein. An epitope may also comprise amino acids, which are not located sequentially within the amino acid sequence of a protein.

In a particular embodiment, said antibody is a monoclonal antibody chosen in the group consisting of:
A monoclonal antibody comprising a heavy chain comprising at least one, preferentially at least two, preferentially three, of CDR-H1, CDR-H2 and CDR-H3 of amino acid sequences SEQ ID N° 4, 5 and 6, respectively, or sequences with at least 80%, preferably 85%, 90%, 95% and 98% identity after optimal alignment with sequences SEQ ID N° 4, 5 and 6, respectively, and a light chain comprising at least one, preferentially at least two, preferentially three, of CDR-L1, CDR-L2 and CDR-L3 of amino acid sequences SEQ ID N° 7, 8 and 9, respectively, or sequences with at least 80%, preferably 85%, 90%, 95% and 98% identity after optimal alignment with sequences SEQ ID N° 7, 8 and 9, respectively, A monoclonal antibody comprising a heavy chain comprising at least one, preferentially at least two, preferentially three, of CDR-H1, CDR-H2 and CDR-H3 of amino acid sequences SEQ ID N° 10, 11 and 12, respectively, or sequences with at least 80%, preferably 85%, 90%, 95% and 98% identity after optimal alignment with sequences SEQ ID N° 10, 11 and 12, respectively, and a light chain comprising at least one, preferentially at least two, preferentially three, of CDR-L1, CDR-L2 and CDR-L3 of amino acid sequences SEQ ID N° 13, 14 and 15, respectively, or sequences with at least 80%, preferably 85%, 90%, 95% and 98% identity after optimal alignment with sequences SEQ ID N° 13, 14 and 15, respectively, A monoclonal antibody comprising a heavy chain comprising at least one, preferentially at least two, preferentially three, of CDR-H1, CDR-H2 and CDR-H3 of amino acid sequences SEQ ID N° 16, 17 and 18, respectively, or sequences with at least 80%, preferably 85%, 90%, 95% and 98% identity after optimal alignment with sequences SEQ ID N° 16, 17 and 18, respectively, and a light chain comprising at least one, preferentially at least two, preferentially three, of CDR-L1, CDR-L2 and CDR-L3 of amino acid sequences SEQ ID N° 19, 20 and 21, respectively, or sequences with at least 80%, preferably 85%, 90%, 95% and 98% identity after optimal alignment with sequences SEQ ID N° 19, 20 and 21, respectively, A monoclonal antibody comprising a heavy chain comprising at least one, preferentially at least two, preferentially three, of CDR-H1, CDR-H2 and CDR-H3 of amino acid sequences SEQ ID N° 22, 23 and 24, respectively, or sequences with at least 80%, preferably 85%, 90%, 95% and 98% identity after optimal alignment with sequences SEQ ID N° 22, 23 and 24, respectively, and a light chain comprising at least one, preferentially at least two, preferentially three, of CDR-L1, CDR-L2 and CDR-L3 of amino acid sequences SEQ ID N° 25, 26 and 27, respectively, or sequences with at least 80%, preferably 85%, 90%, 95% and 98% identity after optimal alignment with sequences SEQ ID N° 25, 26 and 27, respectively, A monoclonal antibody comprising a heavy chain comprising at least one, preferentially at least two, preferentially at least three, of CDR-H1, CDR-H2 and CDR-H3 of amino acid sequences SEQ ID N° 28, 29 and 30, respectively, or sequences with at least 80%, preferably 85%, 90%, 95% and 98% identity after optimal alignment with sequences SEQ ID N° 28, 29 and 30, respectively, and a light chain comprising at least one, preferentially at least two, preferentially three, of CDR-L1, CDR-L2 and CDR-L3 of amino acid sequences SEQ ID N° 31, 32 and 33, respectively, or sequences with at least 80%, preferably 85%, 90%, 95% and 98% identity after optimal alignment with sequences SEQ ID N° 31, 32 and 33, respectively, and A monoclonal antibody comprising a heavy chain comprising at least one, preferentially at least two, preferentially three, of CDR-H1, CDR-H2 and CDR-H3 of amino acid sequences SEQ ID N° 34, 35 and 36, respectively, or sequences with at least 80%, preferably 85%, 90%, 95% and 98% identity after optimal alignment with sequences SEQ ID N° 34, 35 and 36, respectively, and a light chain comprising at least one, preferentially at least two, preferentially three, of CDR-L1, CDR-L2 and CDR-L3 of amino acid sequences SEQ ID N° 37, 38 and 39, respectively, or sequences with at least 80%, preferably 85%, 90%, 95% and 98% identity after optimal alignment with sequences SEQ ID N° 37, 38 and 39, respectively.

As used herein, the "percentage identity" or "% identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of methods known by a man skilled in the art.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated.

In another particular embodiment, the antibody used in the method of the invention is a humanised antibody.

As used herein, the expression "humanized antibody" means an antibody that contains CDR regions derived from an antibody of nonhuman origin, the other parts of the antibody molecule being derived from one or several human antibodies. In addition, some of the skeleton segment residues (called FR for framework) can be modified to preserve binding affinity, according to techniques known by a man skilled in the art (Jones et al., Nature, 321:522-525, 1986). The goal of humanisation is a reduction in the immunogenicity of a xenogenic antibody, such as a murine antibody, for introduction into a human, while maintaining the full antigen binding affinity and specificity of the antibody.

The humanized antibodies of the invention or fragments of same can be prepared by techniques known to a person skilled in the art (such as, for example, those described in the documents Singer et al., J. Immun., 150:2844-2857, 1992). Such humanized antibodies are preferred for their use in methods involving in vitro diagnoses or preventive and/or therapeutic treatment in vivo. Other humanization techniques are also known to the person skilled in the art. Indeed, Antibodies can be humanized using a variety of techniques including CDR-grafting (EP 0 451 261; EP 0682 040; EP 0939 127; EP 0566 647; U.S. Pat. Nos. 5,530,101; 6,180,370; 5,585,089; 5,693,761; 5,639,641; 6,054,297; 5,886,152; and 5,877,293), veneering or resurfacing (EP 0 592 106; EP 0 519 596; Padlan E. A., 1991, Molecular Immunology 28(4/5): 489-498; Studnicka G. M. et al., 1994, Protein Engineering 7(6): 805-814; Roguska M.A. et al., 1994, Proc. Natl. Acad. ScL U.S.A., 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741.

In a more particular embodiment, said antibody is a humanized antibody selected in the group consisting of:

A humanized antibody comprising a heavy chain comprising at least one, preferentially at least two, preferentially three, of CDR-H1, CDR-H2 and CDR-H3 of amino acid sequences SEQ ID N° 4, 5 and 6, respectively, or sequences with at least 80%, preferably 85%, 90%, 95% and 98% identity after optimal alignment with sequences SEQ ID N° 4, 5 and 6, respectively, and a light chain comprising at least one, preferentially at least two, preferentially three, of CDR-L1, CDR-L2 and CDR-L3 of amino acid sequences SEQ ID N° 7, 8 and 9, respectively, or sequences with at least 80%, preferably 85%, 90%, 95% and 98% identity after optimal alignment with sequences SEQ ID N° 7, 8 and 9, respectively, A humanized antibody comprising a heavy chain comprising at least one, preferentially at least two, preferentially three, of CDR-H1, CDR-H2 and CDR-H3 of amino acid sequences SEQ ID N° 10, 11 and 12, respectively, or sequences with at least 80%, preferably 85%, 90%, 95% and 98% identity after optimal alignment with sequences SEQ ID N° 10, 11 and 12, respectively, and a light chain comprising at least one, preferentially at least two, preferentially three, of CDR-L1, CDR-L2 and CDR-L3 of amino acid sequences SEQ ID N° 13, 14 and 15, respectively, or sequences with at least 80%, preferably 85%, 90%, 95% and 98% identity after optimal alignment with sequences SEQ ID N° 13, 14 and 15, respectively, A humanized antibody comprising a heavy chain comprising at least one, preferentially at least two, preferentially three, of CDR-H1, CDR-H2 and CDR-H3 of amino acid sequences SEQ ID N° 16, 17 and 18, respectively, or sequences with at least 80%, preferably 85%, 90%, 95% and 98% identity after optimal alignment with sequences SEQ ID N° 16, 17 and 18, respectively, and a light chain comprising at least one, preferentially at least two, preferentially three, of CDR-L1, CDR-L2 and CDR-L3 of amino acid sequences SEQ ID N° 19, 20 and 21, respectively, or sequences with at least 80%, preferably 85%, 90%, 95% and 98% identity after optimal alignment with sequences SEQ ID N° 19, 20 and 21, respectively, A humanized antibody comprising a heavy chain comprising at least one, preferentially at least two, preferentially three, of CDR-H1, CDR-H2 and CDR-H3 of amino acid sequences SEQ ID N° 22, 23 and 24, respectively, or sequences with at least 80%, preferably 85%, 90%, 95% and 98% identity after optimal alignment with sequences SEQ ID N° 22, 23 and 24, respectively, and a light chain comprising at least one, preferentially at least two, preferentially three, of CDR-L1, CDR-L2 and CDR-L3 of amino acid sequences SEQ ID N° 25, 26 and 27, respectively, or sequences with at least 80%, preferably 85%, 90%, 95% and 98% identity after optimal alignment with sequences SEQ ID N° 25, 26 and 27, respectively, A humanized antibody comprising a heavy chain comprising at least one, preferentially at least two, preferentially three, of CDR-H1, CDR-H2 and CDR-H3 of amino acid sequences SEQ ID N° 28, 29 and 30, respectively, or sequences with at least 80%, preferably 85%, 90%, 95% and 98% identity after optimal alignment with sequences SEQ ID N° 28, 29 and 30, respectively, and a light chain comprising at least one, preferentially at least two, preferentially three, of CDR-L1, CDR-L2 and CDR-L3 of amino acid sequences SEQ ID N° 31, 32 and 33, respectively, or sequences with at least 80%, preferably 85%, 90%, 95% and 98% identity after optimal alignment with sequences SEQ ID N° 31, 32 and 33, respectively, and A humanized antibody comprising a heavy chain comprising at least one, preferentially at least two, preferentially three, of CDR-H1, CDR-H2 and CDR-H3 of amino acid sequences SEQ ID N° 34, 35 and 36, respectively, or sequences with at least 80%, preferably 85%, 90%, 95% and 98% identity after optimal alignment with sequences SEQ ID N° 34, 35 and 36, respectively, and a light chain comprising at least one, preferentially at least two, preferentially three, of CDR-L1, CDR-L2 and CDR-L3 of amino acid sequences SEQ ID N° 37, 38 and 39, respectively, or sequences with at least 80%, preferably 85%, 90%, 95% and 98% identity after optimal alignment with sequences SEQ ID N° 37, 38 and 39, respectively, wherein said antibody also comprises constant regions of the light-chain and the heavy-chain derived from a human antibody.

In a first embodiment, a method according to the invention comprises contacting a biological sample with an anti-hPG antibody binding to an epitope of hPG, wherein said epitope is located within the C-terminal part of hPG or to an epitope located within the N-terminal part of hPG.

In a more specific embodiment, a method according to the invention comprises contacting a biological sample with an anti-hPG antibody binding to an epitope of hPG, wherein said epitope includes an amino acid sequence corresponding to an amino acid sequence of the N-terminal part of progastrin chosen among an amino acid sequence corresponding to amino acids 10 to 14 of hPG, amino acids 9 to 14 of hPG, amino acids 4 to 10 of hPG, amino acids 2 to 10 of hPG and amino acids 2 to 14 of hPG, wherein the amino acid sequence of hPG is SEQ ID N° 1.

In a more specific embodiment, a method according to the invention comprises contacting a biological sample with an anti-hPG antibody binding to an epitope of hPG, wherein said epitope includes an amino acid sequence corresponding to an amino acid sequence of the C-terminal part of progastrin, chosen among an amino acid sequence corresponding to amino acids 71 to 74 of hPG, amino acids 69 to 73 of hPG, amino acids 71 to 80 of hPG (SEQ ID N° 40), amino acids 76 to 80 of hPG, and amino acids 67 to 74 of hPG, wherein the amino acid sequence of hPG is SEQ ID N° 1.

In a first embodiment, a composition according to the invention comprises an antibody recognizing an epitope including an amino acid sequence corresponding to an amino acid sequence of progastrin.

In a more specific embodiment, a composition according to the invention comprises an antibody recognizing an epitope of progastrin wherein said epitope includes an amino acid sequence corresponding to an amino acid sequence of the N-terminal part of progastrin, wherein said amino acid sequence may include residues 10 to 14 of hPG, residues 9 to 14 of hPG, residues 4 to 10 of hPG, residues 2 to 10 of hPG or residues 2 to 14 of hPG, wherein the amino acid sequence of hPG is SEQ ID N° 1.

In a more specific embodiment, a composition according to the invention comprises an antibody recognizing an epitope of progastrin wherein said epitope includes an amino acid sequence corresponding to an amino acid sequence of the C-terminal part of progastrin, wherein said amino acid sequence may include residues 71 to 74 of hPG, residues 69 to 73 of hPG, residues 71 to 80 of hPG (SEQ ID N° 40), residues 76 to 80 of hPG, or residues 67 to 74 of hPG, wherein the amino acid sequence of hPG is SEQ ID N° 1.

In a particular embodiment of a method for the in vitro diagnosis of ovarian cancer according to the invention, said method comprises a step of contacting a biological sample from a subject with a first molecule which binds to a first part of progastrin and with a second molecule which binds to a second part of progastrin. In a more particular embodiment, wherein said progastrin-binding molecule is an antibody, a biological sample from a subject is contacted with an antibody which binds to a first epitope of progastrin and with a second antibody which binds to a second epitope of progastrin.

In a preferred embodiment, the method of the present invention for the diagnosis of ovarian cancer comprises the detection of progastrin in a biological sample from a human subject.

In a more preferred embodiment, the method of the present invention for the diagnosis of ovarian cancer comprises the detection of the concentration of progastrin in a biological sample from a human subject.

In another particular embodiment, the method of the present invention for the diagnosis of ovarian cancer comprises the detection of the concentration of progastrin in a biological sample from a human subject, wherein said biological sample is selected from blood, serum and plasma.

In a further preferred embodiment, the method of the present invention comprises contacting a sample from said subject with an anti-hPG antibody as described above, wherein the binding of said anti-hPG antibody in the sample indicates the presence of ovarian cancer in said subject.

In a more particular embodiment, the method of the present invention comprises contacting sample from said subject with an anti-hPG antibody as described above, wherein a concentration of progastrin superior to 5 pM in said sample is indicative of the presence of ovarian cancer in said subject.

More preferably, the method of the present invention comprises contacting a sample from said subject with an anti-hPG antibody as described above, wherein a concentration of progastrin superior to 5 pM, 10 pM, 20 pM, 30 pM or 40 pM in said sample is indicative of the presence of ovarian cancer in said subject.

Still more preferably, the method of the present invention comprises contacting a sample from said subject with an anti-hPG antibody as described above, wherein a concentration of progastrin superior to 5 pM, 10 pM, 20 pM, 30 pM, 40 pM in said plasma is indicative of the presence of metastasized ovarian cancer in said subject The present invention also relates to methods for monitoring the efficacy of a treatment for ovarian cancer in a patient, such as chemotherapy, biological therapy, immunotherapy or antibody therapy, by determining the concentration of progastrin in a first sample, such as a bodily fluid or biopsy of ovarian cancer, obtained from a patient before treatment for ovarian cancer, and then comparing the concentration of progastrin in the first sample to that in a second sample obtained from the same patient after treatment, where a reduction in the concentration of progastrin in said second sample compared to said first sample indicates that the treatment was effective.

In a particular embodiment, a method according to the invention comprises comparing the concentration of progastrin in a biological sample obtained from a patient with a predetermined value of concentration of progastrin in the sample, in a more particular embodiment, said predetermined value is chosen among: an mean, or average, of sample values based on the mean, or average, determination of the value in a population free of ovarian cancer, a progastrin concentration value obtained when the patient was known to be free of ovarian cancer.

In a particular embodiment, a method according to the invention for the in vitro diagnosis of ovarian cancer comprises the determination of progastrin concentration in a sample from said patient and a second diagnosis test of ovarian cancer. In a more particular embodiment, a method according to the invention for the in vitro diagnosis of ovarian cancer comprises the determination of progastrin concentration in a sample from said patient and a second diagnosis test of ovarian cancer, wherein In a particular embodiment of the invention, a method according to the present invention comprises the determination of the level of progastrin over time in samples from a patient who has been or is being treated for ovarian cancer.

In another aspect, the subject matter of the present invention relates to a composition for use in the prevention or the treatment of ovarian cancer, wherein said composition comprises a progastrin-binding antibody, or an antigen-binding fragment thereof.

Antibody compositions for use in the methods of the invention can be prepared as different formulations, including, but not limited to, an aqueous suspension, for administration by a variety of routes, including, but not limited to, parenteral, intrathecal, subcutaneous, intravenous, intramuscular, intraperitoneal, infusion or bolus administration. In some embodiments, the composition is formulated for parenteral administration, and in some specific embodiments, intravenous injection by infusion.

In a particular embodiment, a composition for use in the prevention or the treatment of ovarian cancer, according to the invention, comprises an effective dose the anti-progastrin antibodies of the invention ranges from 0.001 mg/kg to about 250 mg/kg, which may be given in one administration, or over multiple, spaced administrations.

In a particular embodiment, a composition for use in the prevention or the treatment of ovarian cancer, according to the invention, comprises a progastrin-binding antibody, or an antigen-binding fragment thereof selected among polyclonal antibodies, monoclonal antibodies, chimeric antibodies, single chain antibodies, camelized antibodies, IgA1 antibodies, IgA2 antibodies, IgD antibodies, IgE antibodies, IgG1 antibodies, IgG2 antibodies, IgG3 antibodies, IgG4 antibodies and IgM antibodies.

Preferably, said antibodies are those described above. More preferably, said antibodies are humanized antibodies.

In a more particular embodiment, a composition for use in the prevention or the treatment of ovarian cancer, according to the invention, comprises a progastrin-binding antibody, or an antigen-binding fragment thereof which has an affinity for progastrin of at least 5000 nM, at least 500 nM, 100 nM, 80 nM, 60 nM, 50 nM, 40 nM, 30 nM, 20 nM, 10 nM, 7 nM, 5 nM, 4 nM, 3 nM, 2 nM, 1 nM, 0.5 nM, 0.1 nM, 50 pM, 10 pM, 5 pM, 1 pM, or at least 0.1 pM, as determined by a method such as above-described.

In an even more particular embodiment, a composition for use in the prevention or the treatment of ovarian cancer comprises a progastrin-binding antibody, wherein said progastrin-binding molecule, or an antigen-binding fragment thereof, is a neutralizing antibody.

The expression "neutralizing anti-PG antibody" designates an antibody that binds PG and blocks PG-dependent signaling, resulting in the inhibition of PG-induced responses in tumor cells, and particularly in ovarian tumor cells. Inhibiting PG-induced responses of ovarian cells may be mediated by repression of cell differentiation, repression of cell death, and/or stimulation of cell proliferation.

In another particular embodiment, a composition for use in the prevention or the treatment of ovarian cancer comprises a progastrin-binding antibody, wherein said progastrin-binding molecule, or an antigen-binding fragment thereof, is a humanized antibody.

In a particular embodiment, a composition for use in the prevention or the treatment of ovarian cancer comprises a progastrin-binding antibody, wherein said progastrin-binding antibody, or an antigen-binding fragment thereof, is conjugated to a cytotoxic agent.

In another particular embodiment, a composition for use in the prevention or the treatment of ovarian cancer for a patient comprises a progastrin-binding antibody, wherein said patient has been diagnosed with ovarian cancer by a method according to the present invention, wherein a concentration of progastrin is higher in a biological sample from said patient than in a reference sample.

In a more particular aspect, the present invention relates to a composition for use in the prevention or the treatment of ovarian cancer according to the invention, wherein said progastrin-binding antibody, or an antigen-binding fragment thereof, is selected among N-terminal anti-progastrin antibodies and C-terminal anti-progastrin antibodies.

In another aspect, the present invention relates to a pharmaceutical composition comprising a composition for use in the prevention or the treatment of ovarian cancer according to the invention, and a pharmaceutically acceptable carrier. More specifically, the pharmaceutical composition for use in the prevention or the treatment of ovarian cancer according to the invention, comprises an antibody as described above and a pharmaceutically acceptable carrier.

In a more particular aspect, the present invention relates to a pharmaceutical composition comprising a composition for use in the prevention or the treatment of ovarian cancer according to the invention, and a pharmaceutically acceptable carrier, wherein said anti-progastrin antibody is administered at a dose from 0.001 mg/kg to 250 mg/kg, and preferably at a dose of at least 0.005 mg/kg, at least 0.01 mg/kg, at least 0.05 mg/kg, at least 0.1 mg/kg, at least 0.5 mg/kg, at least 1 mg/kg, at least 5 mg/kg, at least 10 mg/kg, at least 50 mg/kg or at least 100 mg/kg. In another aspect, the present invention relates to a kit of parts comprising a composition for use in the prevention or the treatment of ovarian cancer, according to the invention, and an anti-cancer therapeutic molecule.

Indeed, treatment with anti-PG monoclonal antibodies as described herein can be combined with, or adjunctive to, other therapy. Non-limiting examples of other therapy include chemotherapeutic treatment, radiation therapy, surgical resection, and antibody therapy.

In another aspect, the present invention relates to a kit of part comprising a composition for use in the prevention or the treatment of ovarian cancer, according to the invention, and an anti-cancer therapeutic molecule chosen among: a chemotherapeutic molecule, a targeted therapy molecule.

In a particular embodiment, the present invention relates to kits of part comprising, for the simultaneous, sequential or separate administration, a composition for the treatment of ovarian cancer according to the invention and a chemotherapeutic molecule. Useful chemotherapeutic molecules for this purpose, include, but are not limited to folate antagonists, purine antagonists, pyrimidine antagonists, DNA alkylating molecules, DNA cross-linking drugs, antibiotics, platinum complexes, proteasome inhibitors, mitotic spindle poisons, topoisomerase inhibitors, tyrosine kinase inhibitors, and others.

In another particular embodiment, the present invention relates to kits of part comprising, for the simultaneous, sequential or separate administration, a composition according to the invention and a composition comprising another targeted therapy molecule. Such targeted therapy molecule include, but are not limited to antibodies that target EGFR, such as cetuximab or panitumumab, antibodies that target VEGF, such as bevacizumab, antibodies that target HER2, such as trastuzumab or pertuzumab, antibodies that target PD-1 and PDL-1, such as pembrolizumab, antibodies that target CTLA-4, such as ipilimumab, small molecule drugs that target EGFR, such as erlotinib, small molecule drugs that target BRAF, such as vemurafenib or dabrafenib, a recombinant fusion protein that target VEGF, such as Aflibercept.

In another particular aspect, the present invention relates to the use of a progastrin-binding antibody, or an antigen-binding fragment thereof, for the diagnosis of ovarian cancer.

In another particular aspect, the present invention relates to the use of a progastrin-binding antibody, or an antigen-binding fragment thereof, for the prevention or the treatment of ovarian cancer.

In a more particular aspect, the present invention relates to the use of a progastrin-binding antibody, or an antigen-binding fragment thereof, for the prevention or the treatment of ovarian cancer for a patient, wherein the concentration of progastrin in a biological sample of said patient has been determined and is higher than the concentration of progastrin of a reference biological sample.

In a more particular aspect, the present invention relates to the use of a progastrin-binding antibody, or an antigen-binding fragment thereof, for the prevention or the treatment of ovarian cancer for a patient, wherein said patient presents metastasis.

In an even more particular aspect, the present invention relates to the use of a progastrin-binding antibody, or an antigen-binding fragment thereof, for the prevention or the treatment of ovarian cancer for a patient, wherein said patient presents metastasis and wherein the concentration of progastrin in a biological sample of said patient has been determined and is higher than the concentration of progastrin of a reference biological sample.

The constituents of which the combination is composed may be administered simultaneously, separately, or sequentially so as to obtain the maximum efficacy of the combination; it being possible for each administration to vary in its duration from a rapid administration to a continuous perfusion.

As used herein, "simultaneous administration" refers to the administration of the two compounds of the composition according in a single and unique pharmaceutical form. As used herein, "separate administration" refers to the administration, at the same time, of the two compounds of the composition according to the invention in distinct pharmaceutical forms. As used herein, "sequential administration" refers to the successive administration of the two compounds of the composition according to the invention, each in a distinct pharmaceutical form.

A "therapeutically effective amount", as used herein, refers to the minimum concentration or amount of a compound (or of compounds), which is effective to prevent, alleviate, reduce or ameliorate symptoms of disease or prolong the survival of the patient being treated.

The characteristics of the embodiments of the invention will become further apparent from the following detailed description of examples below.

FIGURE LEGEND

FIG. 1: median plasmatic concentration of progastrin in ovarian cancer patients (n=8), and in control patients (n=103).

Figure 2:
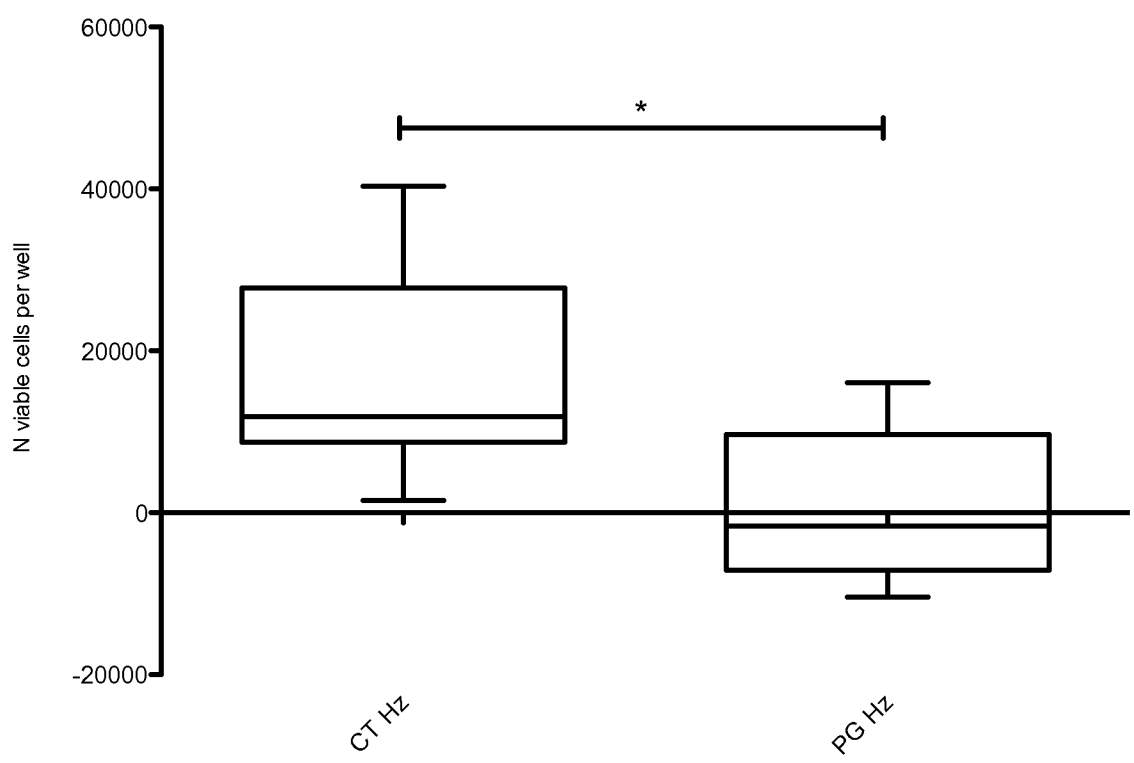

FIG. 2: Cell counts for SK-OV-3 cells after treatment for 48 h with 20 pg/ml of humanized control antibodies (anti-human FcG1, from BioXCell)(CT Hz), or with 20 pg/ml anti-hPG Hz (PG Hz)—Two-tailed t-test, * p<0.05.

Figure 3:
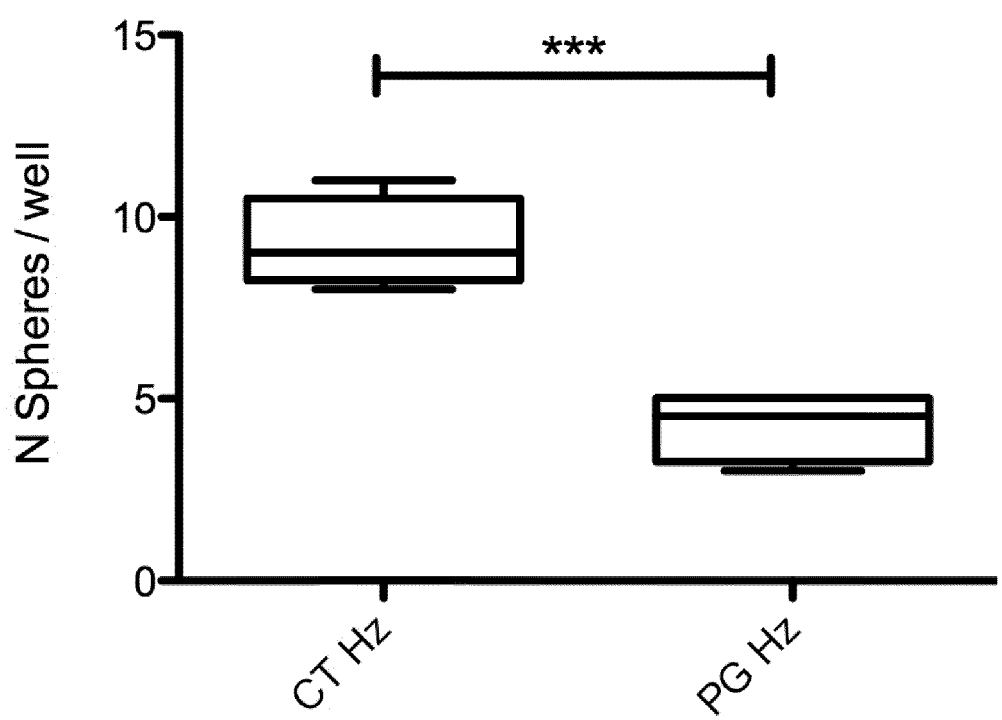

FIG. 3: Number of SK-OV-3 spheres formed following treatment with control (CT Hz) or anti-PG humanized antibody (PG Hz) under ultra-low adherent conditions—Two-tailed t-test, *** p<0.001.

EXAMPLES

Example 1: Detection of Plasmatic Progastrin Concentration Using Polyclonal Antibodies Plasma progastrin levels were quantified by ELISA through the use of two specific anti-progastrin antibodies: capture antibodies are coated on the wells of the plate, whereas revelation antibodies are used to detect progastrin and mediates revelation of the signal.

In the present example, quantification is based on the ELISA method which allows, through the use of a substrate whose reaction emits light, to assign a value proportional to the luminescence amount of antibodies bound to the antigen retained by capture antibodies.

Material

Reagents and apparatus are listed in Table 7:

TABLE 7

| Designation | Provider | Référence |
|---|---|---|
| Plates MaxiSORP white Nunc, 96 wells | Dutscher | # 055221 |
| Sodium Carbonate/Bicarbonate | Sigma | # 21851 |
| DPBS 1X | Lonza | # P04-36500 |
| TWEEN® 20 | Biosolve | # 20452335 |
| BSA | Euromedex | # 04-100-810-C |
| Streptavidin-HRP | Pierce (Thermo) | # 21130 |
| SuperSignal ELISA Femto Maximum Sensitivity Substrate | Pierce (Thermo) | # 37074 |
| Anti-ProGastrin Polyclonal Antibody | Eurogentec | / |

Polyclonal antibodies were obtained by immunizing a rabbit with N-terminal progastrin (SEQ ID N° 2) or with C-terminal progastrin corresponding to amino acids 71 to 80 of hPG and having the sequence FGRRSAEDEN (SEQ ID N° 40), according to standard protocols.

The binding characteristics of polyclonal antibodies against progastrin used in this assay are the following: absence of binding to G34-Gly, G34, G17-Gly, G17, binding to full length progastrin.

96 wells plates are coated by preparing a solution of carbonate—sodium bicarbonate, 50 mM pH 9.6 by dissolving the contents of one capsule in 100 ml of MilliQ water. A solution of capture antibody (3 pg/ml), corresponding to polyclonal antibodies obtained by using the C-terminal of progastrin FGRRSAEDEN (SEQ ID N° 40) is prepared in carbonate buffer. 100 microliters of antibodies solution is added to each well and incubated at 4° C. for 16 hours (1 night). Plates are then blocked by eliminating the antibodies solution and wash 3 times with 300 ul 1×PBS/0.1% TWEEN®-20, then adding 200 μl of blocking buffer (1×PBS/0.1% TWEEN®-20/0.1% BSA) per well, and incubated 2 hours at 22° C. Blocking buffer is then eliminated, wells are washed 3 times with 300 μl 1×PBS/0.1% TWEEN®-20.

Plasma dilution is performed as follows: The plasma is used pure, diluted 1/2, 1/5 and 1/10. Dilutions are prepared from pure plasma in 1×PBS/0.1% Tween 20/0.1% BSA.

For the control test, ELISA in the presence of a known concentration of progastrin, progastrin dilution is prepared as follows: stock recombinant PG (Full length human progastrin produced in *E. coli* and affinity purified with Glutathione agarose/Tag removal (Tev)/IMAC Counter purification/dialysis, from Institut Pasteur, Paris, France) is prepared at a concentration of 0.45 mg/ml (45 microM), in triplicate.

Ranges of progastrin concentrations were prepared as follows:

Solution A: Pre-dilution 1/10, 2 μl of stock+18 μl of the buffer
Solution B: Pre-dilution 1/100, 10 μl of A+90 μl of the buffer
Solution C: Pre-dilution 1/1000, 10 μl of B+90 μl of the buffer
Solution D: 500 pM, 5.55 μl of C+494.5 μl of the diluent
Solution E: 250 pM, 250 μl of D+250 μl of the diluent
Solution F: 100 pM, 200 μl of E+300 μl of the diluent
Solution G: 50 pM, 250 μl of F+250 μl of the diluent
Solution H: 25 pM, 200 μl of G+200 μl of the diluent
Solution I: 10 pM, 100 μl of H+150 μl of the diluent The range of recombinant PG is linear and can therefore be more or less extensive according to the antibody used.

For the preparation of test samples, approximately 500 μl of each sample are set aside and stored until analysis (and confirmation if necessary) of the results. 100 μl of each point of the range and/or plasmas are assayed pure, diluted to 1/2, 1/5 and 1/10, and incubated for 2 hours at 22° C. on the plates.

For the revelation of the test, the plates are washed 3 times with 300 μl 1×PBS/0.1% TWEEN®-20. A solution of the polyclonal rabbit anti-progastrin antibody, wherein said antibodies have been obtained by using the N-terminal part of progastrin as an immunogen, coupled to biotin to 0.5 μg/ml, is prepared by dilution in 1×PBS/0.1% TWEEN®-20/0.1% BSA. 100 μl of this solution is added to each well. Incubation takes place for 1 hour at 22° C. The revelation with streptavidin-HRP is performed by removing detection antibody and wash 3 times with 300 μl 1×PBS/0.1% TWEEN®-20, then preparing a solution of Streptavidin-HRP at 20 ng/ml diluted in 1×PBS/0.1% TWEEN®-20/0.1% BSA, wherein 100 Add 100 μl of this solution is added to each well, before incubation for 1 hour at 22° C.

The detection consists of eliminating streptavidin-HRP and wash 3 times with 300 μl 1×PBS/0.1% TWEEN®-20, then adding 100 μl of chemiluminescent substrate solution per well. The substrate solution is prepared by mixing equal volumes of the two solutions SuperSignal ELISA Femto kit, 20 ml+20 ml, 30 minutes before use and stored at room temperature in the dark. Luminescence is read after 5 minutes incubation at room temperature in the dark.

For each condition, the test is performed in triplicate and the results of the ranges will be presented as a graph showing the change in luminescence depending on the progastrin concentration. For each plasma dilution, the concentration of progastrin is determined using the equation of the linear regression line of the corresponding range (range 1/10th for a sample diluted to 1/10th).

Methods and Results

The median plasmatic concentration of progastrin is 8.45 pM in patients having ovarian cancer (n=8), whereas the median plasmatic concentration of progastrin is 0 pM in control patients (n=103) (FIG. 1). These data demonstrate that patients with ovarian cancer had higher concentrations of progastrin in their plasma compared to healthy control individuals.

These data demonstrate that patients with ovarian cancer have higher levels of progastrin in their plasma compared to healthy control individuals.

Example 2: Detection of Progastrin Concentration Using Monoclonal Anti-Progastrin Antibodies The wells of Nunc MaxiSORP 96-well plates are coated with a first progastrin-specific antibody as follows. Anti-progastrin monoclonal antibodies specific for the carboxy-terminal region of progastrin are diluted to a concentration of 3 pg/ml in a solution of 50 mM, pH 9.6 sodium carbonate/bicarbonate buffer in MilliQ water.

A total of 100 μl of the antibody solution is then added to each well of the 96-well plates, and incubated overnight at 4° C. After binding, the antibody solution is removed from the wells, which are then washed three times with 100 μl wash buffer (IX PBS/0.1% TWEEN®-20). A total of 100 μl blocking buffer (IX PBS/0.1% TWEEN®-20/0.1% BSA) is then added to each well and incubated for 2 hours at 22° C. Blocking buffer is then removed and the wells washed three times with wash buffer. Plasma or serum samples isolated from patients is then added to the wells in a volume of 100 μl in a dilution series, typically 1:1, 1:2, 1:5 and 1:10 dilutions, and is then incubated for 2 hours at 22° C. Plasma or serum samples are analyzed in duplicate.

Assays also include two standard curves. The first standard curve is prepared using dilutions of recombinant progastrin to a final amount of 1 ng, 0.5 ng, 0.25 ng, 0.1 ng, 0.05 ng, 0.01 ng, and 0 ng per well. The second standard curve, which serves as a negative control, is prepared from progastrin-negative human serum diluted in blocking buffer at the same dilutions as the test samples, i.e., 1:1, 1:2, 1:5 and 1:10. Alternatively, when plasma samples are being assayed, the second standard curve, which serves as a negative control, is prepared from progastrin-negative human plasma diluted in blocking buffer at the same dilutions as the test samples, i.e., 1:1, 1:2, 1:5 and 1:10.

After incubation with the plasma or serum samples is complete, the well contents are removed and the wells are washed three times with wash buffer, 100 μl/well, after which progastrin bound to the first antibody is detected using a second antibody specific for progastrin, as follows.

Biotin-coupled anti-progastrin monoclonal antibodies specific for the amino-terminal region of progastrin are diluted in blocking buffer to a concentration of 0.1 to 10 μl g/ml, depending on the antibody. A total of 100 μl of the antibody solution is then added to each well, and incubated for 1 hour at 22° C.

After secondary antibody binding is complete, the plates are washed three times with wash buffer, 100 ul/well, after which 100 ul of a solution of streptavidin-HRP (25 ng/ml in blocking buffer) is added to each well and incubated for 1 hour at 22° C. After incubation with the streptavidin-HRP solution is complete, the plates are washed three times with wash buffer, 100 μl/well. Thereafter, 100 μl of chemiluminescent substrate prepared using a Pierce SuperSignal ELISA Femto Maximum Sensitivity Chemiluminescent Substrate kit, is added per well, incubated for 5 min at room temperature in the dark, and then read on a luminometer.

Based on the luminometer readings, linear regression analysis is used to derive the equation of the lines corresponding to the standard curve data. Using this equation, the concentration of progastrin in the various patient samples is then calculated.

The median plasmatic concentration of progastrin is calculated in patients having ovarian cancer and compared to the median plasmatic concentration of progastrin in plasma of control patients. These data demonstrate that patients with ovarian cancer had elevated levels of progastrin in their plasma compared to healthy control individuals.

Example 3: Neutralizing Activity of Anti-hPG Antibodies on Cancer Cell Lines 3.1. Neutralizing Activity of Anti-hPG Monoclonal Antibodies PA-1, Caov-3, SW626, ES-2, and SK-OV-3 are cell lines commonly used to study ovarian cancer, which produce and secrete progastrin. Monoclonal antibodies to PG are tested for their ability to inhibit proliferation in these different cell lines. Survival of cells from each Caov-3, ES-2, SK-OV-3, KATO-III, AGS, and MGC-803 cell line is tested using different anti-hPG monoclonal antibodies.

For each experiment, 50,000 cells are seeded into 6-well plates in medium containing fetal calf serum and incubated for 8 hours. Cells are serum-starved overnight, and starting at 24 hours after seeding (time "T0"), cells are treated in sextuplicates every 12 h for 48 hours, in the absence of fetal calf serum, with 1 to 20 pg/ml of monoclonal control antibodies (monoclonal antibody anti-puromycin)(CT mAb), or with 1 to 20 pg/ml anti-hPG mAb, wherein said mAb is a C-terminal anti-hPG monoclonal antibody or a N-terminal anti-hPG monoclonal antibody.

Said mAb is a C-terminal anti-hPG antibody, selected among:

An antibody comprising a heavy chain comprising CDR-H1, CDR-H2 and CDR-H3 of amino acid sequences SEQ ID N° 28, 29 and 30, and a light chain comprising CDR-L1, CDR-L2 and CDR-L3 of amino acid sequences SEQ ID N° 31, 32 and 33, An antibody comprising a heavy chain comprising CDR-H1, CDR-H2 and CDR-H3 of amino acid sequences SEQ ID N° 34, 35 and 36, and a light chain comprising CDR-L1, CDR-L2 and CDR-L3 of amino acid sequences SEQ ID N° 37, 38 and 39.

or a N-terminal anti-hPG antibody selected among:

An monoclonal antibody comprising a heavy chain comprising CDR-H1, CDR-H2 and CDR-H3 of amino acid sequences SEQ ID N° 4, 5 and 6, respectively, and a light chain comprising CDR-L1, CDR-L2 and CDR-L3 of amino acid sequences SEQ ID N° 7, 8 and 9, An antibody comprising a heavy chain comprising CDR-H1, CDR-H2 and CDR-H3 of amino acid sequences SEQ ID N° 10, 11 and 12, respectively, and a light chain comprising CDR-L1, CDR-L2 and CDR-L3 of amino acid sequences SEQ ID N° 13, 14 and 15, respectively, An antibody comprising a heavy chain comprising CDR-H1, CDR-H2 and CDR-H3 of amino acid sequences SEQ ID N° 16, 17 and 18, respectively, and a light chain comprising CDR-L1, CDR-L2 and CDR-L3 of amino acid sequences SEQ ID N° 19, 20 and 21, respectively, An antibody comprising a heavy chain comprising CDR-H1, CDR-H2 and CDR-H3 of amino acid sequences SEQ ID N° 22, 23 and 24, respectively, and a light chain comprising CDR-L1, CDR-L2 and CDR-L3 of amino acid sequences SEQ ID N° 25, 26 and 27, respectively, The number of cells at T0 is counted in a control well, for each experiment.

Specifically, the number of live cells in both control and anti-hPG mAb treated wells is counted at 48 hours, then the difference between each cell count and the cell count determined at T0, is calculated. The resulting number of anti-hPG mAb-treated cells is then expressed as a percentage of the number of control mAb-treated cells.

Treatment with anti-hPG monoclonal antibodies reduces cell number as compared to treatment with control antibody. Statistical significance is determined using a one-way ANOVA with a Tukey post-hoc test: *=p<0.05, =p<0.01, and *=p<0.001. In each cell line, anti-hPG antibodies reduce cell survival.

3.2. Neutralizing Activity of Anti-hPG Humanized Antibodies on Cell Survival

Humanized antibodies to PG are tested for their ability to inhibit proliferation of PA-1, Caov-3, SW626, ES-2 and SK-OV-3 cell lines. Survival of cells from PA-1, Caov-3, SW626, ES-2 and SK-OV-3 cell lines is tested using different anti-hPG humanized antibodies.

For each experiment, 80,000 cells are seeded into 6-well plates in medium containing fetal calf serum and incubated for 8 hours. Cells are serum-starved overnight, and starting at 24 hours after seeding (time "T0"), cells are treated in sextuplicates every 12 h for 48 hours, in the absence of fetal calf serum, with 20 pg/ml of humanized control antibodies (anti-human FcG1, from BioXCell) (CT Hz), or with 20 pg/ml anti-hPG Hz (PG Hz), wherein said Hz is a C-terminal anti-hPG humanized antibody or a N-terminal anti-hPG humanized antibody. The number of cells at T0 is counted in a control well, for each experiment.

Specifically, the number of live cells in both control and anti-hPG Hz treated wells is counted at 48 hours, then the difference between each cell count and the cell count determined at T0, is calculated.

Treatment with anti-hPG Hz antibodies reduces cell number as compared to treatment with control antibody.

3.3. Neutralizing Activity of Anti-hPG Monoclonal Antibodies on Cancer Stem Cell Frequency Monoclonal antibodies to PG are tested for their ability to reduce cancer stem cell (CSC) frequency in PA-1, Caov-3, SW626, ES-2 and SK-OV-3 cell lines using Extreme Limiting Dilution Assay (ELDA). CSC frequency from each PA-1, Caov-3, SW626, ES-2 and SK-OV-3 cell line is tested using different anti-hPG monoclonal antibodies.

For each experiment, cells are seeded in ultra-low attachment (ULA) P96 (96-well plates) at fixed cellular concentrations per well using a FACS Aria flow cytometer, and a range of concentrations is used from one to 500 cells per well. The cells are cultivated for up to 11 days in ULA plates with M11 medium (Macari et al, Oncogene, 2015) and treated every 3 or 4 days with 1 to 20 µg/ml of monoclonal control antibodies (monoclonal antibody anti-puromycin) (CT mAb), or with 1 to 20 pg/ml anti-hPG mAb, wherein said mAb is a C-terminal anti-hPG monoclonal antibody or a N-terminal anti-hPG monoclonal antibody Specifically, at the end of the incubation phase, the plates are observed with a phase-contrast microscope and the number of positive wells per cellular concentration is assessed. Finally, the ELDA webtool is used to calculate the CSC frequencies of each treatment group and test for any statistical difference between groups (modified Chi-square test).

Treatment with anti-hPG monoclonal antibodies reduces CSC frequency as compared to treatment with control antibody.

3.4. Neutralizing Activity of Anti-hPG Humanized Antibodies on Cancer Stem Cell Frequency Sphere Formation Assay Humanized antibodies to PG are tested for their ability to reduce cancer stem cell (CSC) frequency in Caov-3, ES-2 and SK-OV-3 cell line using sphere formation assay.

For each experiment, 500 cells are seeded in 24-well ultra-low attachment (ULA). The cells are cultivated for up to 10 days in ULA plates with M11 medium (Macari et al, Oncogene, 2015) and treated every 3 or 4 days with 20 pg/ml of humanized control antibodies (anti-human FcG1, from BioXCell)(CT Hz), or with 20 pg/ml anti-hPG Hz (PG Hz), wherein said Hz is a C-terminal anti-hPG humanized antibody or a N-terminal anti-hPG humanized antibody.

Specifically, at the end of the incubation phase, the wells are photographed via brightfield microscopy, the pictures are analyzed and the spheres with a mean diameter above 30 µm are counted.

Treatment with anti-hPG humanized antibodies reduces CSC frequency as compared to treatment with control antibody.

Extreme Limiting Dilution Assay

Humanized antibodies to PG are tested for their ability to reduce cancer stem cell (CSC) frequency in PA-1, Caov-3, SW626 and SK-OV-3 cell lines using Extreme Limiting Dilution Assay (ELDA). CSC frequency from each PA-1, Caov-3, SW626 and SK-OV-3 cell line is tested using different anti-hPG humanized antibodies.

For each experiment, cells are seeded in ultra-low attachment (ULA) P96 (96-well plates) at fixed cellular concentrations per well using a FACS Aria flow cytometer, and a range of concentrations is used from one to 500 cells per well. The cells are cultivated for up to 11 days in ULA plates with M11 medium (Macari et al, Oncogene, 2015) and treated every 3 or 4 days with 1 to 20 pg/ml of humanized control antibodies (anti-human FcG1, from BioXCell)(CT Hz), or with 1 to 20 pg/ml anti-hPG Hz, wherein said Hz is a C-terminal anti-hPG humanized antibody or a N-terminal anti-hPG humanized antibody.

Specifically, at the end of the incubation phase, the plates are observed with a phase-contrast microscope and the number of positive wells per cellular concentration is assessed. Finally, the ELDA webtool is used to calculate the CSC frequencies of each treatment group and test for any statistical difference between groups (modified Chi-square test).

Treatment with anti-hPG humanized antibodies reduces CSC frequency as compared to treatment with control antibody.

3.5. Neutralizing Activity of Anti-hPG Monoclonal Antibodies on the WNT/β-Catenin Pathway PA-1, Caov-3, SW626, ES-2 and SK-OV-3 are cell lines commonly used to study ovarian cancer, which produce and secrete progastrin. Monoclonal antibodies to PG were tested for their ability to inhibit the WNT/β-catenin pathway in these different cell lines using the expression of the protein survivin, a well-known WNT/β-catenin pathway targeted gene, as read-out. Survivin expression from each PA-1, Caov-3, SW626, ES-2 and SK-OV-3 cell line is tested using different anti-hPG monoclonal antibodies.

For each experiment, 50,000 cells are seeded into 6-well plates in medium containing fetal calf serum and incubated for 8 hours. Cells are serum-starved overnight, and starting 24 hours after seeding cells are treated in quadruplicate every 12 h for 72 hours, in the absence of fetal calf serum, with 1 to 20 μg/ml of monoclonal control antibodies (monoclonal antibody anti-puromycin)(CT mAb), or with 1 to 20 pg/ml anti-hPG mAb, wherein said mAb is a C-terminal anti-hPG monoclonal antibody or a N-terminal anti-hPG monoclonal antibody.

Specifically, after 72 hours of treatment, cells are harvested and total proteins are extracted using RIPA buffer. An equal amount of protein from CT mAb or anti-hPG mAb treated cells are then subjected to a western blot using anti-survivin antibody (monoclonal antibody, #2802 from Cell Signaling) and anti-actin antibody as loading control (monoclonal antibody, #A4700 from SIGMA). Quantification is performed using the GBOX chemi system from Syngene.

Treatment with anti-hPG monoclonal antibodies reduces survivin expression as compared to treatment with control antibody. Statistical significance is determined using a unpaired Student's T-test: *=p<0.05, =p<0.01, and *=p<0.001.

3.6. Neutralizing Activity of Anti-hPG Humanized Antibodies on the WNT/β-Catenin Pathway Humanized antibodies to PG are tested for their ability to inhibit the WNT/β-catenin pathway in PA-1, Caov-3, SW626, ES-2 and SK-OV-3 cell lines using the expression of the protein survivin, a well-known WNT/β-catenin pathway targeted gene, as read-out. Survivin expression from each PA-1, Caov-3, SW626, ES-2 and SK-OV-3 cell line is tested using different anti-hPG humanized antibodies.

For each experiment, 50,000 cells are seeded into 6-well plates in medium containing fetal calf serum and incubated for 8 hours. Cells are serum-starved overnight, and starting 24 hours after seeding cells are treated in quadruplicate every 12 h for 72 hours, in the absence of fetal calf serum, with 1 to 20 pg/ml of humanized control antibodies (anti-human FcG1, from BioXCell)(CT Hz), or with 1 to 20 pg/ml anti-hPG Hz, wherein said Hz is a C-terminal anti-hPG humanized antibody or a N-terminal anti-hPG humanized antibody.

Specifically, after 72 hours of treatment, cells are harvested and total proteins are extracted using RIPA buffer. An equal amount of protein from CT Hz or anti-hPG Hz treated cells are then subjected to a western blot using anti-survivin antibody (monoclonal antibody, #2802 from Cell Signaling) and anti-actin antibody as loading control (monoclonal antibody, #A4700 from SIGMA). Quantification is performed using the GBOX chemi system from Syngene.

Treatment with anti-hPG humanized antibodies reduces survivin expression as compared to treatment with control antibody. Statistical significance is determined using a unpaired Student's T-test: *=p<0.05, =p<0.01, and *=p<0.001.

The invention claimed is:

1. A method for inhibiting the proliferation of ovarian cancer stem cells in a patient in need thereof, said method comprising administering a composition comprising a monoclonal progastrin-binding antibody, or an antigen-binding fragment thereof, to said patient,
wherein said antigen-binding fragment thereof comprises the 6 complementary determining regions (CDR) of the monoclonal progastrin-binding antibody from which it is derived and wherein said CDRs are defined by the international ImMungoGenTics information system (IMGT), and
wherein said monoclonal progastrin-binding antibody is selected from the group consisting of:
an antibody comprising a heavy chain (H) comprising CDR-H1, CDR-H2 and CDR-H3 comprising amino acid sequences SEQ ID NO:4, SEQ ID NO:5, and SEQ ID NO:6, respectively, and a light chain (L) comprising CDR-L1, CDR-L2 and CDR-L3 comprising amino acid sequences SEQ ID NO:7, SEQ ID NO:8, and SEQ ID NO:9, respectively,
an antibody comprising a heavy chain comprising CDR-H1, CDR-H2 and CDR-H3 comprising amino acid sequences SEQ ID NO:10, SEQ ID NO:11, and SEQ ID NO:12, respectively, and a light chain comprising CDR-L1, CDR-L2 and CDR-L3 comprising amino acid sequences SEQ ID NO:13, SEQ ID NO:14, and SEQ ID NO:15, respectively,
an antibody comprising a heavy chain comprising CDR-H1, CDR-H2 and CDR-H3 comprising amino acid sequences SEQ ID NO:16, SEQ ID NO:17, and SEQ ID NO:18, respectively, and a light chain comprising CDR-L1, CDR-L2 and CDR-L3 comprising amino acid sequences SEQ ID NO:19, SEQ ID NO:20, and SEQ ID NO:21, respectively,
an antibody comprising a heavy chain comprising CDR-H1, CDR-H2 and CDR-H3 comprising amino acid sequences SEQ ID NO:22, SEQ ID NO:23, and SEQ ID NO:24, respectively, and a light chain comprising CDR-L1, CDR-L2 and CDR-L3 comprising amino acid sequences SEQ ID NO:25, SEQ ID NO:26, and SEQ ID NO:27, respectively,
an antibody comprising a heavy chain comprising CDR-H1, CDR-H2 and CDR-H3 comprising amino acid sequences SEQ ID NO:28, SEQ ID NO:29, and SEQ ID NO:30, respectively, and a light chain comprising CDR-L1, CDR-L2 and CDR-L3 comprising amino acid sequences SEQ ID NO:31, SEQ ID NO:32, and SEQ ID NO:33, respectively, and
an antibody comprising a heavy chain comprising CDR-H1, CDR-H2 and CDR-H3 comprising amino acid sequences SEQ ID NO:34, SEQ ID NO:35, and SEQ ID NO:36, respectively, and a light chain comprising CDR-L1, CDR-L2 and CDR-L3 comprising amino acid sequences SEQ ID NO:37, SEQ ID NO:38, and SEQ ID NO:39, respectively.

2. The method of claim 1, wherein said monoclonal progastrin-binding antibody, or antigen-binding fragment thereof, is selected from the group consisting of humanized antibodies, single chain antibodies, immunoglobulin (Ig) A1 (IgA1) antibodies, IgA2 antibodies, IgD antibodies, IgE antibodies, IgG1 antibodies, IgG2 antibodies, IgG3 antibodies, IgG4 antibodies, and IgM antibodies.

3. The method of claim 1, wherein said monoclonal progastrin-binding antibody is a humanized antibody.

4. The method of claim 1, wherein said monoclonal progastrin-binding antibody, or an antigen-binding fragment thereof, is conjugated to a cytotoxic molecule.

5. The method of claim 1, further comprising the simultaneous, sequential, or separate administration of a chemotherapeutic molecule selected from the group consisting of folate antagonists, purine antagonists, pyrimidine antagonists, DNA alkylating molecules, DNA cross-linking drugs, antibiotics, platinum complexes, proteasome inhibitors, mitotic spindle poisons, topoisomerase inhibitors, and tyrosine kinase inhibitors.

6. The method of claim 1, further comprising the simultaneous, sequential or separate administration of a targeted therapy molecule selected in the group consisting of: antibodies that target epidermal growth factor receptor (EGFR), antibodies that target vascular endothelial growth factor (VEGF), antibodies that target human epidermal growth factor receptor (HER2), antibodies that target programmed cell death protein 1 (PD-1) and programmed death-ligand 1 (PDL-1), antibodies that target cytotoxic T-lymphocyte-associated protein 4 (CTLA-4), small molecule drugs that target EGFR, small molecule drugs that target B-Raf Proto-Oncogene Serine/Threonine Kinase (BRAF), and recombinant fusion proteins that target VEGF.

7. The method of claim 6, wherein said antibody that targets EGFR is cetuximab or panitumumab, wherein said antibody that targets VEGF is bevacizumab, wherein said antibody that targets HER2 is trastuzumab or pertuzumab, wherein said antibody that targets PD-1 and PDL-1 is pembrolizumab, wherein said antibody that targets CTLA-4 is ipilimumab, wherein said small molecule drug that targets EGFR is erlotinib, wherein said small molecule drug that targets BRAF is vemurafenib or dabrafenib, and wherein said recombinant fusion protein that targets VEGF is Aflibercept.

8. A method for inhibiting the proliferation of ovarian cancer stem cells in a patient in need thereof, said method comprising administering a pharmaceutical composition comprising a monoclonal progastrin-binding antibody, or an antigen-binding fragment thereof, and a pharmaceutically acceptable carrier, to said patient, wherein said antigen-binding fragment thereof comprises the 6 complementary determining regions (CDR) of the monoclonal progastrin-binding antibody from which it is derived and wherein said CDRs are defined by the international ImMungoGenTics information system (IMGT), and wherein said monoclonal progastrin-binding antibody is selected from the group consisting of:

an antibody comprising a heavy chain (H) comprising CDR-H1, CDR-H2 and CDR-H3 comprising amino acid sequences SEQ ID NO:4, SEQ ID NO:5, and SEQ ID NO:6, respectively, and a light chain (L) comprising CDR-L1, CDR-L2 and CDR-L3 comprising amino acid sequences SEQ ID NO:7, SEQ ID NO:8, and SEQ ID NO:9, respectively, an antibody comprising a heavy chain comprising CDR-H1, CDR-H2 and CDR-H3 comprising amino acid sequences SEQ ID NO:10, SEQ ID NO:11, and SEQ ID NO:12, respectively, and a light chain comprising CDR-L1, CDR-L2 and CDR-L3 comprising amino acid sequences SEQ ID NO:13, SEQ ID NO:14, and SEQ ID NO:15, respectively, an antibody comprising a heavy chain comprising CDR-H1, CDR-H2 and CDR-H3 comprising amino acid sequences SEQ ID NO:16, SEQ ID NO:17, and SEQ ID NO:18, respectively, and a light chain comprising CDR-L1, CDR-L2 and CDR-L3 comprising amino acid sequences SEQ ID NO:19, SEQ ID NO:20, and SEQ ID NO:21, respectively, an antibody comprising a heavy chain comprising CDR-H1, CDR-H2 and CDR-H3 comprising amino acid sequences SEQ ID NO:22, SEQ ID NO:23, and SEQ ID NO:24, respectively, and a light chain comprising CDR-L1, CDR-L2 and CDR-L3 comprising amino acid sequences SEQ ID NO:25, SEQ ID NO:26, and SEQ ID NO:27, respectively, an antibody comprising a heavy chain comprising CDR-H1, CDR-H2 and CDR-H3 comprising amino acid sequences SEQ ID NO:28, SEQ ID NO:29, and SEQ ID NO:30, respectively, and a light chain comprising CDR-L1, CDR-L2 and CDR-L3 comprising amino acid sequences SEQ ID NO:31, SEQ ID NO:32, and SEQ ID NO:33, respectively, and an antibody comprising a heavy chain comprising CDR-H1, CDR-H2 and CDR-H3 comprising amino acid sequences SEQ ID NO:34, SEQ ID NO:35, and SEQ ID NO:36, respectively, and a light chain comprising CDR-L1, CDR-L2 and CDR-L3 comprising amino acid sequences SEQ ID NO:37, SEQ ID NO:38, and SEQ ID NO:39, respectively.

* * * * *